US012558380B2

(12) United States Patent
Lanza et al.

(10) Patent No.: US 12,558,380 B2
(45) Date of Patent: *Feb. 24, 2026

---

(54) PHOTORECEPTORS AND PHOTORECEPTOR PROGENITORS PRODUCED FROM PLURIPOTENT STEM CELLS

(71) Applicant: Astellas Institute for Regenerative Medicine, Westborough, MA (US)

(72) Inventors: Robert P. Lanza, Clinton, MA (US); Wei Wang, Rochester, MN (US); Shi-Jiang Lu, Shrewsbury, MA (US)

(73) Assignee: Astellas Institute for Regenerative Medicine, Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/719,473

(22) Filed: Apr. 13, 2022

(65) Prior Publication Data

US 2022/0347228 A1     Nov. 3, 2022

Related U.S. Application Data

(63) Continuation of application No. 16/367,045, filed on Mar. 27, 2019, now abandoned, which is a continuation of application No. 14/214,598, filed on Mar. 14, 2014, now Pat. No. 10,307,444.

(60) Provisional application No. 61/793,168, filed on Mar. 15, 2013.

(51) Int. Cl.
| | |
|---|---|
| A61K 35/54 | (2015.01) |
| A61K 35/30 | (2015.01) |
| A61K 35/545 | (2015.01) |
| C12N 5/00 | (2006.01) |
| C12N 5/0735 | (2010.01) |
| C12N 5/074 | (2010.01) |
| C12N 5/0793 | (2010.01) |
| C12N 5/0797 | (2010.01) |

(52) U.S. Cl.
CPC ............ *A61K 35/545* (2013.01); *A61K 35/30* (2013.01); *C12N 5/0606* (2013.01); *C12N 5/062* (2013.01); *C12N 5/0623* (2013.01); *C12N 5/0696* (2013.01); *C12N 2500/33* (2013.01); *C12N 2501/105* (2013.01); *C12N 2501/13* (2013.01); *C12N 2501/155* (2013.01); *C12N 2501/235* (2013.01); *C12N 2501/33* (2013.01); *C12N 2501/385* (2013.01); *C12N 2506/02* (2013.01)

(58) Field of Classification Search
CPC .... C12N 5/0621; C12N 5/062; C12N 5/0606; A61K 35/30; A61K 35/545
See application file for complete search history.

(56) References Cited

U.S. PATENT DOCUMENTS

| | | | |
|---|---|---|---|
| 6,465,248 B1 | 10/2002 | Commissiong et al. | |
| 7,531,354 B2 | 5/2009 | Stice et al. | |
| 7,541,186 B2 | 6/2009 | Reh et al. | |
| 7,794,704 B2 | 9/2010 | Klimanskaya | |
| 9,133,435 B2 | 9/2015 | Takahashi et al. | |
| 9,249,390 B2 | 2/2016 | Zhu et al. | |
| 9,458,428 B2* | 10/2016 | Clegg ................. | C12N 5/0621 |
| 10,307,444 B2 | 6/2019 | Lanza et al. | |
| 11,241,460 B2 | 2/2022 | Lanza et al. | |
| 2003/0166276 A1 | 9/2003 | Carpenter et al. | |
| 2010/0105137 A1 | 4/2010 | Takahashi et al. | |
| 2010/0136537 A1 | 6/2010 | Swaroop et al. | |
| 2011/0081719 A1 | 4/2011 | Gamm et al. | |
| 2011/0223140 A1 | 9/2011 | Park et al. | |
| 2014/0004086 A1 | 1/2014 | Paek et al. | |
| 2014/0186309 A1 | 7/2014 | Klassen et al. | |
| 2014/0294778 A1 | 10/2014 | Lanza et al. | |
| 2015/0175964 A1* | 6/2015 | Clegg ................. | C12N 5/0621 |
| | | | 435/405 |
| 2016/0030490 A1 | 2/2016 | Lanza et al. | |
| 2016/0175361 A1 | 6/2016 | Lanza et al. | |
| 2016/0175362 A1 | 6/2016 | Lanza et al. | |
| 2018/0117091 A1 | 5/2018 | Small et al. | |
| 2019/0060370 A1 | 2/2019 | Lanza et al. | |
| 2019/0290701 A1 | 9/2019 | Lanza et al. | |
| 2019/0321414 A1 | 10/2019 | Lanza et al. | |
| 2022/0257663 A1 | 8/2022 | Lanza et al. | |

FOREIGN PATENT DOCUMENTS

| | | |
|---|---|---|
| CN | 102204930 A | 10/2011 |
| CN | 102712900 A | 10/2012 |
| EP | 2383333 B1 | 5/2015 |
| JP | 5441099 B2 | 3/2014 |
| KR | 10-2263956 B1 | 6/2021 |
| WO | WO 1996/030403 A1 | 10/1996 |

(Continued)

OTHER PUBLICATIONS

Lamba et al, Efficient generation of retinal progenitor cells from human embryonic stem cells, PNAS, 2022, pp. 12769-12774.*

(Continued)

*Primary Examiner* — Maria Marvich

(74) *Attorney, Agent, or Firm* — Wolf, Greenfield & Sacks, P.C.

(57) ABSTRACT

Methods are provided for the production of photoreceptor cells and photoreceptor progenitor cells from pluripotent stem cells. Additionally provided are compositions of photoreceptor cells and photoreceptor cells, as well as methods for the therapeutic use thereof. Exemplary methods may produce substantially pure cultures of photoreceptor cells and/or photoreceptor cells.

9 Claims, 28 Drawing Sheets

(56) References Cited

FOREIGN PATENT DOCUMENTS

| WO | WO 9955838 A1 | 11/1999 |
|----|----------------|---------|
| WO | WO 2002/074176 A1 | 9/2002 |
| WO | WO 2002/076386 A2 | 10/2002 |
| WO | WO 2004/007749 A2 | 1/2004 |
| WO | WO 2005/123902 A1 | 12/2005 |
| WO | WO 2007/100692 A2 | 9/2007 |
| WO | WO 2008/045952 A2 | 4/2008 |
| WO | WO 2011/028524 A1 | 3/2011 |
| WO | WO 2011/043591 A2 | 4/2011 |
| WO | WO 2011/055855 A1 | 5/2011 |
| WO | WO 2013/077425 A1 | 5/2013 |
| WO | WO 2013/163296 A1 | 10/2013 |
| WO | WO 2013/183774 A1 | 12/2013 |
| WO | WO 2014/174492 A1 | 10/2014 |
| WO | WO 2015/025967 A1 | 2/2015 |
| WO | WO 2015/068505 A1 | 5/2015 |
| WO | WO 2015/087614 A1 | 6/2015 |
| WO | WO 2015/107738 A1 | 7/2015 |
| WO | WO 2015/109148 A1 | 7/2015 |
| WO | WO 2015/121687 A1 | 8/2015 |
| WO | WO 2016/063986 A1 | 4/2016 |
| WO | WO 2016/160718 A1 | 10/2016 |
| WO | WO 2017/043604 A1 | 3/2017 |
| WO | WO 2017/164992 A1 | 9/2017 |
| WO | WO 2017/176810 A1 | 10/2017 |
| WO | WO 2017/183732 A1 | 10/2017 |
| WO | WO 2018/055131 A1 | 3/2018 |
| WO | WO 2018/097253 A1 | 5/2018 |
| WO | WO 2018/132802 A1 | 7/2018 |
| WO | WO 2018/149985 A1 | 8/2018 |
| WO | WO 2018/154295 A1 | 8/2018 |
| WO | WO 2019/017492 A1 | 1/2019 |
| WO | WO 2019/028088 A1 | 2/2019 |
| WO | WO 2019/032999 A1 | 2/2019 |
| WO | WO 2019/054514 A1 | 3/2019 |
| WO | WO 2019/054515 A1 | 3/2019 |
| WO | WO 2019/138250 A1 | 7/2019 |
| WO | WO 2019/170766 A1 | 9/2019 |
| WO | WO 2019/210320 A2 | 10/2019 |
| WO | WO 2019/217630 A1 | 11/2019 |

OTHER PUBLICATIONS

Meyer et al, Modeling early retinal development with human embryonic and induced pluripotent stem cells, PNAS, 2009, pp. 16698-16703.*

Extended European Search Report mailed Oct. 14, 2016 in connection with Application No. EP 14764825.7.

International Search Report and Written Opinion mailed Jul. 11, 2014 for Application No. PCT/US2014/029790.

International Preliminary Report on Patentability mailed Sep. 24, 2015 in connection with PCT/US2014/029790.

[No Author Listed], ARVO Annual Meeting Abstract Search and Program Planner. BIOSIS [online], BIOSIS Accession No. 2012:522138. May 2011;2011:5989. 1 page.

Agathocleous et al., From progenitors to differentiated cells in the vertebrate retina. Annu Rev Cell Dev Biol. 2009;25:45-69. doi: 10.1146/annurev.cellbio.042308.113259. Abstract Only.

Ahmad, Mash-1 is expressed during ROD photoreceptor differentiation and binds an E-box, E(opsin)-1 in the rat opsin gene. Brain Res Dev Brain Res. Dec. 21, 1995;90(1-2):184-9.

Akagi et al., Requirement of multiple basic helix-loop-helix genes for retinal neuronal subtype specification. J Biol Chem. Jul. 2004; 279;28492-98.

Amirpour et al., Differentiation of human embryonic stem cell-derived retinal progenitors into retinal cells by Sonic hedgehog and/or retinal pigmented epithelium and transplantation into the subretinal space of sodium iodate-injected rabbits. Stem Cells Dev. Jan. 2012;21(1):42-53. doi: 10.1089/scd.2011.0073.

Assawachananont et al., Transplantation of embryonic and induced pluripotent stem cell-derived 3D retinal sheets into retinal degen-erative mice. Stem Cell Reports. Apr. 24, 2014;2(5):662-74. doi: 10.1016/j.stemcr.2014.03.011.

Barber et al., Repair of the degenerate retina by photoreceptor transplantation. Proc Natl Acad Sci U S A. Jan. 2, 2013;110(1):354-9. doi: 10.1073/pnas.1212677110. Epub Dec. 17, 2012.

Barnea-Cramer et al., Function of human pluripotent stem cell-derived photoreceptor progenitors in blind mice. Sci Rep. Jul. 13, 2016;6:29784. doi: 10.1038/srep29784.

Bäumer et al., Retinal pigmented epithelium determination requires the redundant activities of Pax2 and Pax6. Development. Jul. 2003;130(13):2903-15.

Bez et al., Neurosphere and neurosphere-forming cells: morpho-logical and ultrastructural characterization. Brain Research. 2003;993:18-29.

Boucherie et al., Brief report: self-organizing neuroepithelium from human pluripotent stem cells facilitates derivation of photorecep-tors. Stem Cells. Feb. 2013;31(2):408-14. doi: 10.1002/stem.1268.

Brzezinski et al., Ascll expression defines a subpopulation of lineage-restricted progenitors in the mammalian retina. Develop-ment. Aug. 2011;138(16):3519-31. doi: 10.1242/dev.064006. Epub Jul. 19, 2011.

Busskamp et al., Genetic reactivation of cone photoreceptors restores visual responses in retinitis pigmentosa. Science. Jul. 23, 2010;329(5990):413-7. doi: 10.1126/science.1190897. Epub Jun. 24, 2010. Abstract only.

Canto-Soler et al., Stem Cell Sources and Their Potential for the Treatment of Retinal Degenerations. Invest Ophthalmol Vis Sci. Apr. 1, 2016;57(5):ORSFd1-9. doi: 10.1167/iovs.16-19127.

Capowski et al., Reproducibility and staging of 3D human retinal organoids across multiple pluripotent stem cell lines. Development. Jan. 9, 2019;146(1):dev171686(1-29). doi: 10.1242/dev.171686.

Carroll et al., Functional photoreceptor loss revealed with adaptive optics: an alternate cause of color blindness. Proc Natl Acad Sci U S A. Jun. 1, 2004;101(22):8461-6. Epub May 17, 2004.

Chao et al., Transplantation of Human Embryonic Stem Cell-Derived Retinal Cells into the Subretinal Space of a Non-Human Primate. Transl Vis Sci Technol. May 16, 2017;6(3):4(1-13). doi: 10.1167/tvst.6.3.4.

Chung et al., Human embryonic stem cell lines generated without embryo destruction. Cell Stem Cell. Feb. 7, 2008;2(2):113-7. doi: 10.1016/j.stem.2007.12.013.

Collin et al., Deconstructing Retinal Organoids: Single Cell RNA-Seq Reveals the Cellular Components of Human Pluripotent Stem Cell-Derived Retina. Stem Cells. May 2019;37(5):593-598. doi: 10.1002/stem.2963. Epub Jan. 12, 2019.

Collin et al., Using Zinc Finger Nuclease Technology to Generate CRX-Reporter Human Embryonic Stem Cells as a Tool to Identify and Study the Emergence of Photoreceptors Precursors During Pluripotent Stem Cell Differentiation. Stem Cells. Feb. 2016;34(2):311-21. doi: 10.1002/stem.2240. Epub Nov. 26, 2015.

Cornish et al., The role of opsin expression and apoptosis in determination of cone types in human retina. Exp Eye Res. Jun. 2004;78(6):1143-54. Abstract only.

Cramer et al., Translating induced pluripotent stem cells from bench to bedside: application to retinal diseases. Curr Gene Ther. Apr. 2013;13(2):139-51. Review.

Da Silva et al., Smart thermoresponsive coatings and surfaces for tissue engineering: switching cell-material boundaries. Trends Biotechnol. Dec. 2007;25(12):577-83. Epub Nov. 8, 2007. Abstract Only.

Dorgau et al., Laminin γ3 plays an important role in retinal lamination, photoreceptor organisation and ganglion cell differentiation. Cell Death Dis. May 23, 2018;9(6):615(1-13). doi: 10.1038/s41419-018-0648-0.

Eberle et al., Increased integration of transplanted CD73-positive photoreceptor precursors into adult mouse retina. Investigative Opthalmology & Visual Science. Aug. 2011;52:6462-71. doi:10. 1167/iovs.11-7399.

Eberle et al., Subretinal transplantation of MACS purified photo-receptor precursor cells into the adult mouse retina. J Vis Exp. Feb. 22, 2014;(84):e50932. doi: 10.3791/50932.

(56)                    References Cited

OTHER PUBLICATIONS

Eiraku et al., Mouse embryonic stem cell culture for generation of three-dimensional retinal and cortical tissues. Nat Protoc. Dec. 15, 2011;7(1):69-79. doi: 10.1038/nprot.2011.429. Abstract only.

Eiraku et al., Self-organizing optic-cup morphogenesis in three-dimensional culture. Nature. Apr. 7, 2011;472(7341):51-6. doi: 10.1038/nature09941.

Eldred et al., Thyroid hormone signaling specifies cone subtypes in human retinal organoids. Science. Oct. 12, 2018;362(6411):eaau6348(1-8). Supplemental Information Included, 20 pages. doi: 10.1126/science.aau6348.

Felemban et al., Extracellular matrix component expression in human pluripotent stem cell-derived retinal organoids recapitulates retinogenesis in vivo and reveals an important role for IMPG1 and CD44 in the development of photoreceptors and interphotoreceptor matrix. Acta Biomater. Jul. 1, 2018;74:207-221. doi: 10.1016/j.actbio.2018.05.023. Epub May 17, 2018.

Fischer et al., Transdifferentiation of pigmented epithelial cells: a source of retinal stem cells? Dev Neurosci. 2001;23(4-5):268-76. Abstract Only.

Freund et al., Cone-rod dystrophy due to mutations in a novel photoreceptor-specific homeobox gene (CRX) essential for maintenance of the photoreceptor. Cell. Nov. 14, 1997;91(4):543-53. doi: 10.1016/s0092-8674(00)80440-7.

Gagliardi et al., Characterization and Transplantation of CD73-Positive Photoreceptors Isolated from Human iPSC-Derived Retinal Organoids. Stem Cell Reports. Sep. 11, 2018;11(3):665-680. doi: 10.1016/j.stemcr.2018.07.005. Epub Aug. 9, 2018.

Gagliardi et al., Photoreceptor cell replacement in macular degeneration and retinitis pigmentosa: A pluripotent stem cell-based approach. Prog Retin Eye Res. Jul. 2019;71:1-25. doi: 10.1016/j.preteyeres.2019.03.001. Epub Mar. 16, 2019.

Gamm et al., Directed differentiation of human induced pluripotent stem cells: a retina perspective. Regen Med. May 2010;5(3):315-7. doi: 10.2217/rme.10.28.

Gonzalez-Cordero et al., Photoreceptor precursors derived from three-dimensional embryonic stem cell cultures integrate and mature within adult degenerate retina. Nat Biotechnol. Aug. 2013;31(8):741-7. doi: 10.1038/nbt.2643. Epub Jul. 21, 2013.

Gonzalez-Cordero et al., Recapitulation of Human Retinal Development from Human Pluripotent Stem Cells Generates Transplantable Populations of Cone Photoreceptors. Stem Cell Reports. Sep. 12, 2017;9(3):820-837. doi: 10.1016/j.stemcr.2017.07.022. Epub Aug. 24, 2017.

Gouras et al., Reconstruction of degenerate rd mouse retina by transplantation of transgenic photoreceptors. Investigative Opthalmology &Visual Science. Aug. 1992;33:2579-86.

Haider et al., Mutation of a nuclear receptor gene, NR2E3, causes enhanced S cone syndrome, a disorder of retinal cell fate. Nat Genet. Feb. 2000;24(2):127-31. Abstract only.

Hallam et al., Human-Induced Pluripotent Stem Cells Generate Light Responsive Retinal Organoids with Variable and Nutrient-Dependent Efficiency. Stem Cells. Oct. 2018;36(10):1535-1551. doi: 10.1002/stem.2883. Epub Aug. 13, 2018.

Hambright et al., Long-term survival and differentiation of retinal neurons derived from human embryonic stem cell lines in un-immunosuppressed mouse retina. Molec Vis. Apr. 12, 2012;18:920-36.

Hansson et al., Commentary: isolated stem cells—patentable as cultural artifacts? Stem Cells. Jun. 2007;25(6):1507-10. Epub Mar. 8, 2007. Abstract only.

Hartong et al., Retinitis pigmentosa. Lancet. Nov. 18, 2006;368(9549):1795-809. Review. Abstract only.

Harvey et al., The early phase of horizontal optokinetic responses in the pigmented rat and the effects of lesions of the visual cortex. Vision Res. Jun. 1997;37(12):1615-25.

Hirami et al., Generation of retinal cells from mouse and human induced pluripotent stem cells. Neurosci Lett. Jul. 24, 2009;458(3):126-31. doi: 10.1016/j.neulet.2009.04.035. Epub Apr. 18, 2009.

Hsiue et al., A novel strategy for corneal endothelial reconstruction with a bioengineered cell sheet. Transplantation. Feb. 15, 2006;81(3):473-6. Abstract Only.

Hunt et al., 3D culture of human pluripotent stem cells in RGD-alginate hydrogel improves retinal tissue development. Acta Biomater. Feb. 2017;49:329-343. doi: 10.1016/j.actbio.2016.11.016. Epub Nov. 5, 2016.

Ide et al. Structural characterization of bioengineered human corneal endothelial cell sheets fabricated on temperature-responsive culture dishes. Biomaterials. Feb. 2006;27(4):607-14. Epub Aug. 15, 2005. Abstract Only.

Ikeda et al., Generation of Rx+/Pax6+ neural retinal precursors from embryonic stem cells. Proc Natl Acad Sci U S A. Aug. 9, 2005;102(32):11331-6. Epub Aug. 2, 2005.

Inoue et al., Subretinal transplantation of bone marrow mesenchymal stem cells delays retinal degeneration in the RCS rat model of retinal degeneration. Exp Eye Res. Aug. 2007;85(2):234-41. Epub May 6, 2007. Abstract Only.

Iraha et al., Establishment of Immunodeficient Retinal Degeneration Model Mice and Functional Maturation of Human ESC-Derived Retinal Sheets after Transplantation. Stem Cell Reports. Mar. 13, 2018;10(3):1059-1074. doi: 10.1016/j.stemcr.2018.01.032. Epub Mar. 1, 2018.

Jin et al., Integration-free induced pluripotent stem cells derived from retinitis pigmentosa patient for disease modeling. Stem Cells Transl Med. Jun. 2012;1(6):503-9. doi: 10.5966/sctm.2012-0005. Epub Jun. 1, 2012.

Jin et al., Modeling retinal degeneration using patient-specific induced pluripotent stem cells. PLoS One. Feb. 10, 2011;6(2):e17084(1-8). doi: 10.1371/journal.pone.0017084.

Jonas et al., Intravitreal autologous bone marrow-derived mononuclear cell transplantation: a feasibility report. Acta Ophthalmol. Mar. 2008;86(2):225-6. Epub Sep. 26, 2007.

Jung et al., 3D Microstructured Scaffolds to Support Photoreceptor Polarization and Maturation. Adv Mater. Sep. 2018;30(39):e1803550(1-10). Supplemental Information Included, 10 pages. doi: 10.1002/adma.201803550. Epub Aug. 14, 2018.

Kallman et al., Investigating cone photoreceptor development using patient-derived NRL null retinal organoids. Commun Biol. Feb. 21, 2020;3(1):82(1-13). doi: 10.1038/s42003-020-0808-5.

Katoh et al., Blimp1 suppresses Chx10 expression in differentiating retinal photoreceptor precursors to ensure proper photoreceptor development. J Neurosci. 2010;30(19):6515-6526. doi:10.1523/JNEUROSCI.0771-10.2010.

Kelley et al., Retinoic acid promotes differentiation of photoreceptors in vitro. Development. Aug. 1994;120(8):2091-102.

Klassen et al., Multipotent retinal progenitors express developmental markers, differentiate into retinal neurons, and preserve light-mediated behavior. Invest Ophthalmol Vis Sci. Nov. 2004;45(11):4167-73.

Klimanskaya et al., Human embryonic stem cell lines derived from single blastomeres. Nature. Nov. 23, 2006;444(7118):481-5. Erratum in: Nature. Nov. 23, 2006;444(7118):512. Nature. Mar. 15, 2007;446(7133):342.

Koso et al., CD73, a novel cell surface antigen that characterizes retinal photoreceptor precursor cells. Invest Ophthalmol Vis Sci. Nov. 2009;50(11):5411-8. doi: 10.1167/iovs.08-3246. Epub Jun. 10, 2009.

Kuwahara et al., Generation of a ciliary margin-like stem cell niche from self-organizing human retinal tissue. Nat Commun. Feb. 19, 2015;6:6286(1-15). doi: 10.1038/ncomms7286.

Kwan et al., Photoreceptor layer reconstruction in a rodent model of retinal degeneration. Exp Neurol. Sep. 1999;159(1):21-33. Abstract only.

La Torre et al., Production and transplantation of retinal cells from human and mouse embryonic stem cells. Methods Mol Biol. 2012;884:229-46. doi: 10.1007/978-1-61779-848-1_16. Abstract only.

La Torre et al., Conserved microRNA pathway regulates developmental timing of retinal neurogenesis. Proc Natl Acad Sci U S A. Jun. 25, 2013;110(26):E2362-70. doi: 10.1073/pnas.1301837110. Epub Jun. 10, 2013.

Lakowski et al., Cone and rod photoreceptor transplantation in models of the childhood retinopathy Leber congenital amaurosis

(56)          References Cited

OTHER PUBLICATIONS using flow-sorted Crx-positive donor cells. Hum MolGenet. Dec. 1, 2010;19(23):4545-59. doi: 10.1093/hmg/ddq378. Epub Sep. 21, 2010.

Lakowski et al., Effective transplantation of photoreceptor precursor cells selected via cell surface antigen expression. Stem Cells. Sep. 2011;29(9):1391-404. doi: 10.1002/stem.694.

Lamba et al., Efficient generation of retinal progenitor cells from human embryonic stem cells. Proc Natl Acad Sci U S A. Aug. 22, 2006;103(34):12769-74. Epub Aug. 14, 2006.

Lamba et al., Generation, purification and transplantation of photoreceptors derived from human induced pluripotent stem cells. PLoS One. Jan. 20, 2010;5(1):e8763.

Lamba et al., Transplantation of Human Embryonic Stem Cell-Derived Photoreceptors Restores Some Visual Function in Crx-Deficient Mice. Cell Stem Cell. 2009;4:73-9. doi: 10.1016/j.stem.2008.10.015.

Levine et al., Sonic hedgehog promotes rod photoreceptor differentiation in mammalian retinal cells in vitro. J Neurosci. Aug. 15, 1997;17(16):6277-88. doi: 10.1523/JNEUROSCI.17-16-06277.1997.

Li et al., Generation of Retinal Organoids with Mature Rods and Cones from Urine-Derived Human Induced Pluripotent Stem Cells. Stem Cells Int. Jun. 13, 2018;2018:4968658(1-13). doi: 10.1155/2018/4968658.

Li et al., Rapid induction and long-term self-renewal of primitive neural precursors from human embryonic stem cells by small molecule inhibitors. Proc Natl Acad Sci U S A. May 17, 2011;108(20):8299-304. doi: 10.1073/pnas.1014041108. Epub Apr. 27, 2011.

Liu et al., Integrated analysis of DNA methylation and RNA transcriptome during in vitro differentiation of human pluripotent stem cells into retinal pigment epithelial cells. PLoS One. Mar. 17, 2014;9(3):e91416. doi: 10.1371/journal.pone.0091416. eCollection 2014. e91416.

Livne-Bar et al., Chx10 is required to block photoreceptor differentiation but is dispensable for progenitor proliferation in the postnatal retina. Proc Natl Acad Sci U S A. Mar. 28, 2006;103(13):4988-93.

Lolley et al., Linkage of photoreceptor degeneration by apoptosis with inherited defect in phototransduction. Invest Ophthalmol Vis Sci. Feb. 1994;35(2):358-62.

Lund et al., Human embryonic stem cell-derived cells rescue visual function in dystrophic RCS rats. Cloning Stem Cells. 2006 Fall;8(3):189-99.

Luo et al., Human retinal progenitor cell transplantation preserves vision. J Biol Chem. Mar. 7, 2014;289(10):6362-71. doi: 10.1074/jbc.M113.513713. Epub Jan. 9, 2014.

Maclaren et al., Retinal repair by transplantation of photoreceptor precursors. Nature. Nov. 9, 2006;444:203-7. Abstract Only.

Mandai et al., iPSC-Derived Retina Transplants Improve Vision in rd1 End-Stage Retinal-Degeneration Mice. Stem Cell Reports. Jan. 10, 2017;8(1):69-83. doi: 10.1016/j.stemcr.2016.12.008. Erratum in: Stem Cell Reports. Feb. 14, 2017;8(2):489. Erratum in: Stem Cell Reports. Apr. 11, 2017;8(4):1112-1113.

Mcusic et al., Guiding the morphogenesis of dissociated newborn mouse retinal cells and hES cell-derived retinal cells by soft lithography-patterned microchannel PLGA scaffolds. Biomaterials. Feb. 2012;33(5):1396-405. doi: 10.1016/j.biomaterials.2011.10.083. Epub Nov. 23, 2011.

Mellough et al., Efficient stage-specific differentiation of human pluripotent stem cells toward retinal photoreceptor cells. Stem Cells. Apr. 2012;30(4):673-86.

Mellough et al., Signaling Plays an Important Role in the Formation of Three-Dimensional Laminated Neural Retina and Other Ocular Structures From Human Embryonic Stem Cells. Stem Cells. Aug. 2015;33(8):2416-30. doi: 10.1002/stem.2023. Epub May 13, 2015.

Mellough et al., Systematic Comparison of Retinal Organoid Differentiation from Human Pluripotent Stem Cells Reveals Stage Specific, Cell Line, and Methodological Differences. Stem Cells Transl Med. Jul. 2019;8(7):694-706. doi: 10.1002/sctm.18-0267. Epub Mar. 27, 2019.

Merhi-Soussi et al., High yield of cells committed to the photoreceptor fate from expanded mouse retinal stem cells. Stem Cells. Sep. 2006;24(9):2060-70. doi: 10.1634/stemcells.2005-0311. Epub Apr. 27, 2006.

Meyer et al., Embryonic stem cell-derived neural progenitors incorporate into degenerating retina and enhance survival of hostphotoreceptors. Stem Cells. Feb. 2006;24(2):274-83. Epub Aug. 25, 2005.

Meyer et al., Modeling early retinal development with human embryonic and induced pluripotent stem cells. Proc Natl Acad Sci U S A. Sep. 29, 2009;106(39):16698-703. doi: 10.1073/pnas.0905245106. Epub Aug. 25, 2009.

Meyer et al., Optic vesicle-like structures derived from human pluripotent stem cells facilitate a customized approach to retinal disease treatment. Stem Cells. Aug. 2011;29(8):1206-18. doi: 10.1002/stem.674.

Nagy et al., Murine embryonic stem cells. Methods Enzymol. 2006; 418:3-21. Abstract only.

Nakagawa et al., Generation of induced pluripotent stem cells without Myc from mouse and human fibroblasts. Nat Biotechnol. Jan. 2008;26(1):101-6. Epub Nov. 30, 2007. Abstract only.

Nakano et al., Self-formation of optic cups and storable stratified neural retina from human ESCs. Cell Stem Cell. Jun. 14, 2012;10(6):771-785. doi: 10.1016/j.stem.2012.05.009.

Neeley, A Brief History of Spheroids. ThermoFisher Scientific. Aug. 24, 2016. https://www.thermofisher.com/blog/cellculture/a-brief-history-of-spheroids-and-3d-cell-culture/ [last accessed Dec. 28, 2018].

Ng et al., Two transcription factors can direct three photoreceptor outcomes from rod precursor cells in mouse retinal development. J Neurosci. Aug. 3, 2011;31:11118-25.

Nishida et al., Corneal reconstruction with tissue-engineered cell sheets composed of autologous oral mucosal epithelium. N Engl J Med. Sep. 16, 2004;351(12):1187-96.

Nishida et al., Functional bioengineered corneal epithelial sheet grafts from corneal stem cells expanded ex vivo on a temperature-responsive cell culture surface. Transplantation. Feb. 15, 2004;77(3):379-85. Abstract Only.

Osakada et al., In vitro differentiation of retinal cells from human pluripotent stem cells by small-molecule induction. J Cell Sci. Sep. 1, 2009;122(Pt 17):3169-79. doi: 10.1242/jcs.050393. Epub Aug. 11, 2009.

Osakada et al., Stepwise differentiation of pluripotent stem cells into retinal cells. Nat Protoc. 2009;4(6):811-24. doi: 10.1038/nprot.2009.51. Epub May 7, 2009.

Osakada et al., Toward the generation of rod and cone photoreceptors from mouse, monkey and human embryonic stem cells. Nat Biotechnol. Feb. 2008;26(2):215-24. doi: 10.1038/nbt1384. Epub Feb. 3, 2008. Erratum in: Nat Biotechnol. Mar. 2008;26(3):352. Abstract only.

Ovando-Roche et al., Use of bioreactors for culturing human retinal organoids improves photoreceptor yields. Stem Cell Res Ther. Jun. 13, 2018;9(1):156(1-14). Supplemental Information Included, 6 pages. doi: 10.1186/s13287-018-0907-0.

Parameswaran et al., Induced pluripotent stem cells generate both retinal ganglion cells and photoreceptors: therapeutic implications in degenerative changes in glaucoma and age-related macular degeneration. Stem Cells. Apr. 2010;28(4):695-703. doi: 10.1002/stem.320.

Patterson et al., Defining the nature of human pluripotent stem cell progeny. Cell Res. Jan. 2012;22(1):178-93. doi: 10.1038/cr.2011.133. Epub Aug. 16, 2011.

Pearson et al., Restoration of vision after transplantation of photoreceptors. Nature. May 3, 2012;485(7396):99-103. doi: 10.1038/nature10997.

Pearson, Advances in repairing the degenerate retina by rod photoreceptor transplantation. Biotechnol Adv. Mar.-Apr. 2014;32(2):485-91. doi: 10.1016/j.biotechadv.2014.01.001. Epub Jan. 8, 2014.

Phillips et al., A Novel Approach to Single Cell RNA-Sequence Analysis Facilitates In Silico Gene Reporting of Human Pluripotent

(56)         References Cited

OTHER PUBLICATIONS

Stem Cell-Derived Retinal Cell Types. Stem Cells. Mar. 2018;36(3):313-324. doi: 10.1002/stem.2755. Epub Dec. 25, 2017. Erratum in: Stem Cells. Jul. 2018;36(7):1133.

Phillips et al., Generation of a rod-specific NRL reporter line in human pluripotent stem cells. Sci Rep. Feb. 5, 2018;8(1):2370. Supplemental Information Included, 26 pages. doi: 10.1038/s41598-018-20813-3.

Phillips et al., Modeling human retinal development with patient-specific induced pluripotent stem cells reveals multiple roles for visual system homeobox 2. Stem Cells. Jun. 2014;32(6):1480-92. doi: 10.1002/stem.1667.

Punzo et al., Cellular responses to photoreceptor death in the rd1 mouse model of retinal degeneration. Invest Ophthalmol Vis Sci. Feb. 2007;48(2):849-57.

Reh, Photoreceptor Transplantation in Late Stage Retinal Degeneration. Invest Ophthalmol Vis Sci. Apr. 1, 2016;57(5):ORSFg1-7. doi: 10.1167/iovs.15-17659.

Reichman et al., From confluent human iPS cells to self-forming neural retina and retinal pigmented epithelium. Proc Natl Acad Sci USA. Jun. 10, 2014;111(23):8518-23. doi: 10.1073/pnas.1324212111. Epub May 27, 2014.

Reichman et al., Generation of Storable Retinal Organoids and Retinal Pigmented Epithelium from Adherent Human iPS Cells in Xeno-Free and Feeder-Free Conditions. Stem Cells. May 2017;35(5):1176-1188. doi: 10.1002/stem.2586. Epub Feb. 20, 2017.

Reynolds et al., Generation of neurons and astrocytes from isolated cells of the adult mammalian central nervous system. Science. Mar. 27, 1992;255(5052):1707-10.

Schwartz et al., Embryonic stem cell trials for macular degeneration: a preliminary report. Lancet. Feb. 25, 2012;379(9817):713-20. doi: 10.1016/S0140-6736(12)60028-2. Epub Jan. 24, 2012. Abstract only.

Schwartz et al., Human embryonic stem cell-derived retinal pigment epithelium in patients with age-related macular degeneration and Stargardt's macular dystrophy: follow-up of two open-label phase 1/2 studies. Lancet. Feb. 7, 2015;385(9967):509-16. doi: 10.1016/S0140-6736(14)61376-3. Epub Oct. 15, 2014. Abstract only.

Seiler et al., A new immunodeficient pigmented retinal degenerate rat strain to study transplantation of human cells without immuno-suppression. Graefes Arch Clin Exp Ophthalmol. Jul. 2014;252(7):1079-92. doi: 10.1007/s00417-014-2638-y. Epub May 13, 2014.

Shirai et al., Transplantation of human embryonic stem cell-derived retinal tissue in two primate models of retinal degeneration. Proc Natl Acad Sci USA. Jan. 5, 2016;113(1):E81-90. Supplemental Information Included, 8 pages. doi: 10.1073/pnas.1512590113. Epub Dec. 22, 2015.

Singh et al., Characterization of Three-Dimensional Retinal Tissue Derived from Human Embryonic Stem Cells in Adherent Monolayer Cultures. Stem Cells Dev. Dec. 1, 2015;24(23):2778-95. doi: 10.1089/scd.2015.0144. Epub Sep. 10, 2015.

Singh et al., Reversal of end-stage retinal degeneration and restoration of visual function by photoreceptor transplantation. Proc Natl Acad Sci U S A. Jan. 15, 2013;110(3):1101-6. doi: 10.1073/pnas.1119416110. Epub Jan. 3, 2013.

Stingl et al., Artificial vision with wirelessly powered subretinal electronic implant alpha-IMS. Proc Biol Sci. Feb. 20, 2013;280(1757):20130077. doi: 10.1098/rspb.2013.0077. Print Apr. 22, 2013.

Sullivan et al., Introduction. Chapter 4: Derivation of human embryonic stem cell lines. In Human Embryonic Stem Cells: The Practical Handbook. Eds. Stephen Sullivan et al. John Wiley & Sons. Nov. 2007:p. 35.

Sumide et al., Functional human corneal endothelial cell sheets harvested from temperature-responsive culture surfaces. FASEB J. Feb. 2006;20(2):392-4. Epub Dec. 9, 2005. 23 Pages.

Suzuki et al., The simultaneous treatment of MMP-2 stimulants in retinal transplantation enhances grafted cell migration into the host retina. Stem Cells. Nov. 2006;24(11):2406-11. doi: 10.1634/stemcells.2005-0587.

Swaroop et al., Transcriptional regulation of photoreceptor development and homeostasis in the mammalian retina. Nat Rev Neurosci. Aug. 2010;11(8):563-76.

Tomita et al., Mash1 promotes neuronal differentiation in the retina. Genes Cells. Aug. 1996; 1(8):765-74. doi: 10.1111/j.1365-2443.1996.tb00016.x.

Tu et al., Medium- to long-term survival and functional examination of human iPSC-derived retinas in rat and primate models of retinal degeneration. EBioMedicine. Jan. 2019;39:562-574. doi: 10.1016/j.ebiom.2018.11.028. Epub Nov. 28, 2018.

Tucker et al., Patient-specific iPSC-derived photoreceptor precursor cells as a means to investigate retinitis pigmentosa. Elife. Aug. 27, 2013;2:e00824. doi: 10.7554/eLife.00824. 18 pages.

Tucker et al., Transplantation of adult mouse iPS cell-derived photoreceptor precursors restores retinal structure and function in degenerative mice. PLoS One. Apr. 29, 2011;6(4):e18992. doi: 10.1371/journal.pone.0018992. Erratum in: PLoS One. 2015;10(5):e0125947.

Vergara et al., Three-dimensional automated reporter quantification (3D-ARQ) technology enables quantitative screening in retinal organoids. Development. Oct. 15, 2017;144(20):3698-3705. doi: 10.1242/dev.146290. Epub Sep. 4, 2017.

Volkner et al., Retinal Organoids from Pluripotent Stem Cells Efficiently Recapitulate Retinogenesis. Stem Cell Reports. Apr. 12, 2016;6(4):525-538. doi: 10.1016/j.stemcr.2016.03.001. Epub Mar. 31, 2016.

Vunjak-Novakovic et al., Biomimetic platforms for human stem cell research. Cell Stem Cell. Mar. 4, 2011;8(3):252-61. doi: 10.1016/j.stem.2011.02.014.

Wahlin et al., Photoreceptor Outer Segment-like Structures in Long-Term 3D Retinas from Human Pluripotent Stem Cells. Sci Rep. Apr. 10, 2017;7(1):766(1-15). doi: 10.1038/s41598-017-00774-9.

West et al., Defining the integration capacity of embryonic stem cell-derived photoreceptor precursors. Stem Cells. Jul. 2012;30(7):1424-35. doi: 10.1002/stem.1123.

West et al., Development of Stem Cell Therapies for Retinal Degeneration. Cold Spring Harb Perspect Biol. Aug. 3, 2020;12(8):a035683(1-24). doi: 10.1101/cshperspect.a035683.

West et al., Long-term survival of photoreceptors transplanted into the adult murine neural retina requires immune modulation. Stem Cells. Nov. 2010;28(11):1997-2007. doi: 10.1002/stem.520.

Xiao et al., Spatial and temporal expression of short, long/medium, or both opsins in human fetal cones. J Comp Neurol. Oct. 2, 2000;425(4):545-59. Abstract only.

Yanai et al., Differentiation of human embryonic stem cells using size-controlled embryoid bodies and negative cell selection in the production of photoreceptor precursor cells. Tissue Eng Part C Methods. Oct. 2013;19(10):755-64. doi: 10.1089/ten.TEC.2012.0524. Epub Mar. 15, 2013.

Yao et al., XIAP therapy increases survival of transplanted rod precursors in a degenerating host retina. Invest Ophthalmol Vis Sci. Mar. 1, 2011;52(3):1567-72. doi: 10.1167/iovs.10-5998. Print Mar. 2011.

Yi et al., A fibronectin fragment inhibits tumor growth, angiogenesis, and metastasis. Proc Natl Acad Sci U S A. Jan. 16, 2001;98(2):620-4.

Zaghloul et al., Changes in Rx1 and Pax6 activity at eye field stages differentially alter the production of amacrine neurotransmitter subtypes in Xenopus. Mol Vis. 2007;13:86-95. Epub Jan. 26, 2007.

Zhong et al., Generation of three-dimensional retinal tissue with functional photoreceptors from human iPSCs. Nat Commun. Jun. 10, 2014;5:4047(1-14). Supplemental Information Included, 6 pages. doi: 10.1038/ncomms5047.

Zhou et al., Differentiation of human embryonic stem cells into cone photoreceptors through simultaneous inhibition of BMP, TGFβ and Wnt signaling. Development. Oct. 1, 2015;142(19):3294-306. Supplemental Information Included, 12 pages. doi: 10.1242/dev.125385.

Zhu et al., Three-dimensional neuroepithelial culture from human embryonic stem cells and its use for quantitative conversion to retinal pigment epithelium. PLoS One. 2013;8(1):e54552(1-13). doi: 10.1371/journal.pone.0054552. Epub Jan. 24, 2013.

(56)  References Cited

OTHER PUBLICATIONS

Zrenner et al., Subretinal electronic chips allow blind patients to read letters and combine them to words. Proc Biol Sci. May 22, 2011;278(1711):1489-97. doi: 10.1098/rspb.2010.1747. Epub Nov. 3, 2010.

Zwaka et al., A germ cell origin of embryonic stem cells? Development. Jan. 2005;132(2):227-33.

Finkbeiner et al., Single-cell ATAC-seq of fetal human retina and stem-cell-derived retinal organoids shows changing chromatin landscapes during cell fate acquisition. Cell Rep. Jan. 25, 2022;38(4):110294. doi: 10.1016/j.celrep.2021.110294.

Wang et al., Retinal Cell Type DNA Methylation and Histone Modifications Predict Reprogramming Efficiency and Retinogenesis in 3D Organoid Cultures. Cell Rep. Mar. 6, 2018;22(10):2601-2614. doi: 10.1016/j.celrep.2018.01.075.

* cited by examiner

PAX6     RX1     MERGE

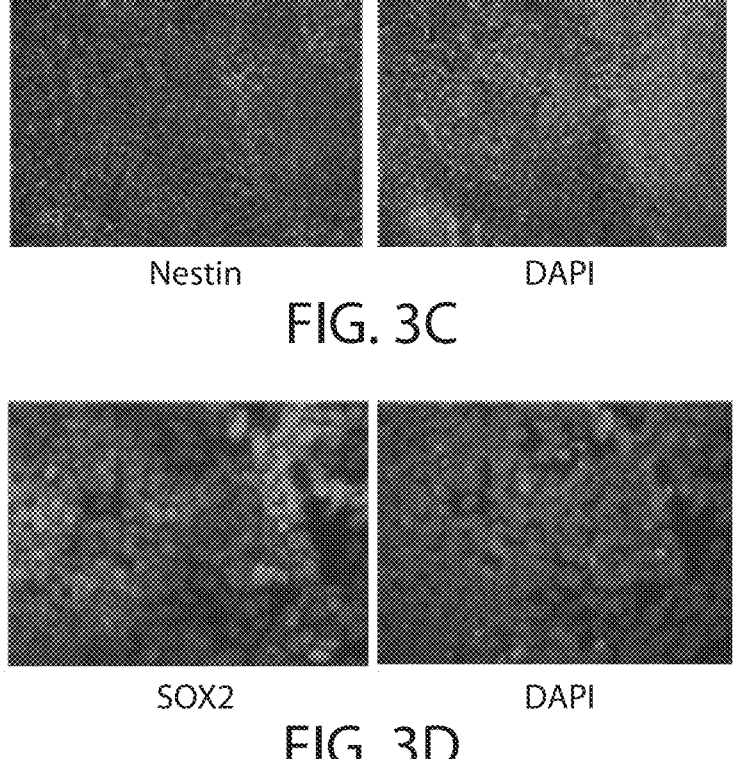
Nestin          DAPI
FIG. 3C
SOX2          DAPI
FIG. 3D
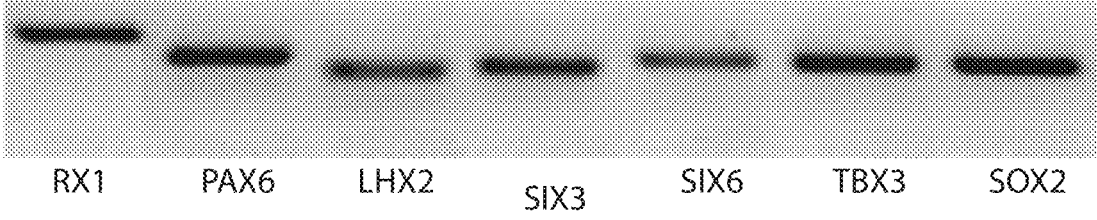
RX1      PAX6      LHX2      SIX3      SIX6      TBX3      SOX2
FIG. 3E

PAX6

CHX10

MERGE

Pax6/CHX10/DAPI

Recoverin/DAPI

Rhodopsin/DAPI

Rhodopsin/Recoverin/DAPI

Opsin (green/red)/DAPI

PDE6a/DAPI

Subretinal Injection: 50,000/eye
Tail Vein Injection: $1 \times 10^6$/mouse
Control: Blank (No cell injection) & PBS

ONL

INL

Tail vein injection: 5 million cells
Intravitreal injection : 200K cells
Control:     1) PBS injection
                  2) No treatment

| DMEM/F12 Components | Molecular Weight | Concentration (mg/L) | mM |
|---|---|---|---|
| Amino Acids | | | |
| Glycine | 75 | 18.75 | 0.25 |
| L-Alanine | 89 | 4.45 | 0.05 |
| L-Arginine hydrochloride | 211 | 147.5 | 0.699 |
| L-Asparagine-H2O | 150 | 7.5 | 0.05 |
| L-Aspartic acid | 133 | 6.65 | 0.05 |
| L-Cysteine hydrochloride-H2O | 176 | 17.56 | 0.0998 |
| L-Cystine 2HCl | 313 | 31.29 | 0.1 |
| L-Glutamic Acid | 147 | 7.35 | 0.05 |
| L-Glutamine | 146 | 365 | 2.5 |
| L-Histidine hydrochloride-H2O | 210 | 31.48 | 0.15 |
| L-Isoleucine | 131 | 54.47 | 0.416 |
| L-Leucine | 131 | 59.05 | 0.451 |
| L-Lysine hydrochloride | 183 | 91.25 | 0.499 |

FIG. 21A

| | | | |
|---|---|---|---|
| L-Methionine | 149 | 17.24 | 0.116 |
| L-Phenylalanine | 165 | 35.48 | 0.215 |
| L-Proline | 115 | 17.25 | 0.15 |
| L-Serine | 105 | 26.25 | 0.25 |
| L-Threonine | 119 | 53.45 | 0.449 |
| L-Tryptophan | 204 | 9.02 | 0.0442 |
| L-Tyrosine disodium salt dihydrate | 261 | 55.79 | 0.214 |
| L-Valine | 117 | 52.85 | 0.452 |
| Vitamins | | | |
| Biotin | 244 | 0.0035 | 1.43E-05 |
| Choline chloride | 140 | 8.98 | 0.0641 |
| D-Calcium pantothenate | 477 | 2.24 | 0.0047 |
| Folic Acid | 441 | 2.65 | 0.00601 |
| Niacinamide | 122 | 2.02 | 0.0166 |
| Pyridoxine hydrochloride | 206 | 2 | 0.00971 |
| Riboflavin | 376 | 0.219 | 0.000582 |
| Thiamine hydrochloride | 337 | 2.17 | 0.00644 |
| Vitamin B12 | 1355 | 0.68 | 0.000502 |
| i-Inositol | 180 | 12.6 | 0.07 |
| Inorganic Salts | | | |
| Calcium Chloride (CaCl2) (anhyd.) | 111 | 116.6 | 1.05 |
| Cupric sulfate (CuSO4-5H2O) | 250 | 0.0013 | 5.2E-06 |
| Ferric Nitrate (Fe(NO3)3-9H2O) | 404 | 0.05 | 0.000124 |
| Ferric sulfate (FeSO4-7H2O) | 278 | 0.417 | 0.0015 |
| Magnesium Chloride (anhydrous) | 95 | 28.64 | 0.301 |
| Magnesium Sulfate (MgSO4) (anhyd.) | 120 | 48.84 | 0.407 |
| Potassium Chloride (KCl) | 75 | 311.8 | 4.16 |

FIG. 21B

| | | | |
|---|---|---|---|
| Sodium Bicarbonate (NaHCO3) | 84 | 1200 | 14.29 |
| Sodium Chloride (NaCl) | 58 | 6995.5 | 120.61 |
| Sodium Phosphate dibasic (Na2HPO4) anhydrous | 142 | 71.02 | 0.5 |
| Sodium Phosphate monobasic (NaH2PO4-H2O) | 138 | 62.5 | 0.453 |
| Zinc sulfate (ZnSO4-7H2O) | 288 | 0.432 | 0.0015 |
| Other Components | | | |
| D-Glucose (Dextrose) | 180 | 3151 | 17.51 |
| HEPES | 238 | 3574.5 | 15.02 |
| Hypoxanthine Na | 159 | 2.39 | 0.015 |
| Linoleic Acid | 280 | 0.042 | 0.00015 |
| Lipoic Acid | 206 | 0.105 | 0.00051 |
| Phenol Red | 376.4 | 8.1 | 0.0215 |
| Putrescine 2HCl | 161 | 0.081 | 0.000503 |
| Sodium Pyruvate | 110 | 55 | 0.5 |
| Thymidine | 242 | 0.365 | 0.00151 |

| Neurobasal Components | Molecular Weight | Concentration (mg/L) | mM |
|---|---|---|---|
| Amino Acids | | | |
| Glycine | 75 | 30 | 0.4 |
| L-Alanine | 89 | 2 | 0.0225 |
| L-Arginine hydrochloride | 211 | 84 | 0.398 |
| L-Asparagine-H2O | 150 | 0.83 | 0.00553 |
| L-Cysteine | 121 | 31.5 | 0.26 |
| L-Histidine hydrochloride-H2O | 210 | 42 | 0.2 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.4 |
| L-Proline | 115 | 7.76 | 0.0675 |
| L-Serine | 105 | 42 | 0.4 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |

FIG. 21C

| Niacinamide | 122 | 4 | 0.0328 |
|---|---|---|---|
| Pyridoxine hydrochloride | 204 | 4 | 0.0196 |
| Riboflavin | 376 | 0.4 | 0.00106 |
| Thiamine hydrochloride | 337 | 4 | 0.0119 |
| Vitamin B12 | 1355 | 0.0068 | 0.000005 |
| i-Inositol | 180 | 7.2 | 0.04 |
| Inorganic Salts | | | |
| Calcium Chloride (CaCl2) (anhyd.) | 111 | 200 | 1.8 |
| Ferric Nitrate (Fe(NO3)3-9H2O) | 404 | 0.1 | 0.000248 |
| Magnesium Chloride (anhydrous) | 95 | 77.3 | 0.814 |
| Potassium Chloride (KCl) | 75 | 400 | 5.33 |
| Sodium Bicarbonate (NaHCO3) | 84 | 2200 | 26.19 |
| Sodium Chloride (NaCl) | 58 | 3000 | 51.72 |
| Sodium Phosphate monobasic (NaH2PO4-H2O) | 138 | 125 | 0.906 |
| Zinc sulfate (ZnSO4-7H2O) | 288 | 0.194 | 0.000674 |
| Other Components | | | |
| D-Glucose (Dextrose) | 180 | 4500 | 25 |
| HEPES | 238 | 2600 | 10.92 |
| Phenol Red | 376.4 | 8.1 | 0.0215 |
| Sodium Pyruvate | 110 | 25 | 0.227 |

| N2 Supplement Components | Molecular Weight | Concentration (mg/L) | mM |
|---|---|---|---|
| Proteins | | | |
| Human Transferrin (Holo) | 10000 | 10000 | 1 |
| Insulin Recombinant Full Chain | 5807.7 | 500 | 0.0861 |
| Other Components | | | |
| Progesterone | 314.47 | 0.63 | 0.002 |
| Putrescine | 161 | 1611 | 10.01 |
| Selenite | 173 | 0.52 | 0.00301 |

FIG. 21D

B27 Components

| Vitamins |
| --- |

Biotin

DL Alpha Tocopherol Acetate
DL Alpha-Tocopherol
Vitamin A (acetate)

| Proteins |
| --- |

BSA, fatty acid free Fraction V
Catalase

Human Recombinant Insulin
Human Transferrin
Superoxide Dismutase

| Other Components |
| --- |

Corticosterone
D-Galactose
Ethanolamine HCl
Glutathione (reduced)
L-Carnitine HCl
Linoleic Acid
Linolenic Acid
Progesterone
Putrescine 2HCl
Sodium Selenite
T3 (triodo-l-thyronine)

FIG. 21E

PHOTORECEPTORS AND PHOTORECEPTOR PROGENITORS PRODUCED FROM PLURIPOTENT STEM CELLS

RELATED APPLICATIONS

This application is a continuation of U.S. application Ser. No. 16/367,045, filed Mar. 27, 2019, which is a continuation of U.S. application Ser. No. 14/214,598, filed Mar. 14, 2014, which claims the benefit under 35 U.S.C. § 119(e) of U.S. Provisional Application Ser. No. 61/793,168, entitled "PHOTORECEPTORS AND PHOTORECEPTOR PROGENITORS PRODUCED FROM PLURIPOTENT STEM CELLS," filed on Mar. 15, 2013, the entire contents of each of which are incorporated herein by reference.

BACKGROUND

Retinal diseases often result in blindness due to loss of post-mitotic neuronal cells. Among the retinal diseases are rod or cone dystrophies, retinal degeneration, retinitis pigmentosa, diabetic retinopathy, macular degeneration, Leber congenital amaurosis and Stargardt disease. In most retinal degenerations, cell loss is primarily in the outer nuclear layer which includes rod and cone photoreceptors. With the loss of post-mitotic neuronal cell populations, an exogenous source of new cells as a replacement for photoreceptor cells is needed.

A potential replacement source of photoreceptor cells includes stem cells. Early studies incorporated the use of mouse cells, mouse stem cells or heterogeneous populations of retinal progenitor cells as a possible source of cells for replacement of lost photoreceptors. These early studies described transplantation of photoreceptor precursor cells from postnatal day 1 mouse retina (Maclaren et al. Nature 444 (9): 203-207, 2006), in vitro generation of retinal precursor cells from mouse embryonic stem cells (Ikeda et al. Proc. Natl. Acad. Sci. 102 (32): 11331-11336, 2005), generation of retinal progenitor cells from postnatal day 1 mouse retinas (Klassen et al. Invest. Ophthal. Vis. Sci. 45 (11): 4167-4175, 2004), implantation of bone marrow mesenchymal stem cells in an RCS rat model of retinal degeneration (Inoue et al. Exp. Eye Res. 8 (2): 234-241, 2007), production of retinal progenitor cells, including ganglion cells, amacrine cells, photoreceptors wherein 0.01% of the total cells expressed S-opsin or rhodopsin, bipolar cells and horizontal cells, from the H1 human embryonic stem cell line (Lamba et al. Proc. Natl. Acad. Sci. 10 (34): 12769-12774, 2006) and induction of induced pluripotent stem cells (iPS) from human fibroblasts to produce retinal progenitor cells (Lamba et al. PLOS ONE 5 (1): e8763. doi: 10.1371/journal.pone.0008763). None of these approaches produced a homogeneous population of photoreceptor progenitor cells or photoreceptor cells for implantation. None of these approaches produced a homogeneous population of photoreceptor progenitor cells or photoreceptor cells that showed in vivo rod or cone function (e.g., detectable by conferring improvements in visual acuity). Supplies of donor-derived tissue from which photoreceptors and photoreceptor progenitors may be isolated (such as cadavers, fetal tissue, and live animals) are limited. Stem cells can be propagated and expanded in vitro indefinitely, providing a potentially inexhaustible source of non-donor derived cells for human therapy. Differentiation of stem cells into a homogeneous population of photoreceptor progenitors or photoreceptors may provide an abundant supply of non-donor derived cells for implantation and treatment of retinal diseases.

BRIEF SUMMARY

In one aspect, the disclosure provides a method of producing eye field progenitor cells, comprising (a) culturing pluripotent stem cells in a retinal induction culture medium. Said pluripotent stem cells may be human.

Said retinal induction culture medium may comprise insulin. Said insulin may be human. Said insulin may be present in a concentration of about 5-50 µg/ml human insulin or about 25 µg/ml.

Said retinal induction culture medium may comprise DMEM/F12, DMEM/high glucose, or DMEM/knock-out. Said retinal induction culture medium may comprise about 450 mg/ml D-glucose or between about 400 and about 500 mg/ml D-glucose.

The retinal induction culture medium may comprise one or more antibiotics. Said antibiotics may include one or both of penicillin and streptomycin, optionally in concentrations of about 100 unit/ml of penicillin and optionally about 100 µg/ml of streptomycin.

The retinal induction culture medium may comprise N2 supplement. Said N2 supplement may be present in a concentration of about 0.1 to 5% or about 1%.

The retinal induction culture medium may comprise B27 supplement. Said B27 supplement may be present in a concentration of about 0.05-2.0% or about 0.2%.

The retinal induction culture medium may comprise non-essential amino acids or MEM non-essential amino acids or glutamine or GlutaMAX™. Said non-essential amino acids or MEM non-essential amino acids may be present in a concentration of about 0.1 mM The retinal induction culture medium may comprise a BMP signaling inhibitor. Said BMP signaling inhibitor may be selected from the group consisting of: Noggin polypeptide, dorsomorphin, LDN-193189, and any combination thereof.

The retinal induction culture medium may comprise Noggin. Said Noggin may be present at a concentration of between about 5-100 ng/ml or about 10-100 ng/ml or about 50 ng/ml.

Said pluripotent stem cells may comprise human ES cells or human iPS cells. Said pluripotent stem cells may be cultured under feeder-free and/or xeno-free conditions prior to being cultured in said retinal induction culture medium comprising insulin, or a cultured on a substrate comprising Matrigel™ and optionally in mTESR1 medium.

Said retinal induction culture medium may be replaced with fresh retinal induction culture medium daily. Said culturing in step (a) may be continued for about 1-10 days or about 2-7 days, or about 5-6 days.

The method may further comprise (b) culturing the cells in a neural differentiation medium. Said neural differentiation medium may comprise Neurobasal medium. Said neural differentiation medium may comprise about 450 mg/ml D-glucose or between about 400 and about 500 mg/ml D-glucose.

The neural differentiation medium may comprise one or more antibiotics. Said antibiotics may include one or both of penicillin and streptomycin, optionally in concentrations of about 100 unit/ml of penicillin and optionally about 100 µg/ml of streptomycin.

The neural differentiation medium may comprise N2 supplement. Said N2 supplement may be present in a concentration of about 0.1 to 5% or about 2%.

The neural differentiation medium may comprise B27 supplement. Said B27 supplement may be present in a concentration of about 0.05-5.0%, about 0.05-2.0% or about 2%.

The neural differentiation medium may comprise non-essential amino acids or MEM non-essential amino acids or glutamine or GlutaMAX™. Said non-essential amino acids or MEM non-essential amino acids may be present in a concentration of about 0.1 mM The neural differentiation culture medium may comprise a BMP signaling inhibitor. Said BMP signaling inhibitor may be selected from the group consisting of: Noggin polypeptide, dorsomorphin, LDN-193189, and any combination thereof.

The neural differentiation culture medium may comprise Noggin. Said Noggin may be present at a concentration of between about 10-100 ng/ml or about 50 ng/ml.

Said cells may be cultured in said neural differentiation medium for about 10-60 days or about 15-35 days or about 24 days.

Said eye field progenitor cells may comprise at least 50%, at least 75%, at least 85%, at least 95%, at least 99% or about 100% of the cells in said culture. Said eye field progenitor cells express one or both of the PAX6 and RX1 markers, and thus may be PAX6 (+) and/or RX1 (+). Said eye field progenitor cells may be one or more of SIX3 (+), SIX6 (+), LHX2 (+), TBX3 (+), and/or Nestin (+). Said eye field progenitor cells may be one or more of SOX2 (+) and OCT4 (–) and NANOG (–).

The method may further comprise differentiating said eye field progenitor cells into retinal neural progenitor cells.

Said eye field progenitor cells may be human.

In another aspect, the disclosure provides a composition comprising eye field progenitor cells produced using a method as described herein, e.g., as described in the preceding paragraphs. In another aspect, the disclosure provides a composition comprising eye field progenitor cells, which are optionally human.

Said eye field progenitor cells may comprise at least 50%, at least 75%, at least 85%, at least 95%, at least 99% or about 100% of the cells in said culture. Said eye field progenitor cells express one or both of the PAX6 and RX1 markers, and thus may be PAX6 (+) and/or RX1 (+). Said eye field progenitor cells may be one or more of SIX3 (+), SIX6 (+), LHX2 (+), TBX3 (+), and/or Nestin (+). Said eye field progenitor cells may be one or more of SOX2 (+) and OCT4 (–) and NANOG (–).

Said eye field progenitor cells may be cryopreserved.

In another aspect, the disclosure provides a method of treatment of an individual in need thereof, comprising administering a composition comprising eye field progenitor cells (e.g., a composition as described herein or a composition produced using a method as described herein) to said individual. Said composition may be administered to the eye, subretinal space, or intravenously.

In another aspect, the disclosure provides a method of producing retinal neural progenitor cells or photoreceptor progenitor cells, comprising (a) culturing eye field progenitor cells in a neural differentiation medium.

Said neural differentiation medium may comprise Neurobasal medium. Said neural differentiation medium may comprise about 450 mg/ml D-glucose or between about 400 and about 500 mg/ml D-glucose.

The neural differentiation medium may comprise one or more antibiotics. Said antibiotics may include one or both of penicillin and streptomycin, optionally in concentrations of about 100 unit/ml of penicillin and optionally about 100 μg/ml of streptomycin.

The neural differentiation medium may comprise N2 supplement. Said N2 supplement may be present in a concentration of about 0.1 to 5% or about 2%.

The neural differentiation medium may comprise B27 supplement. Said B27 supplement may be present in a concentration of about 0.05-5.0%, about 0.05-2.0% or about 2%.

The neural differentiation medium may comprise non-essential amino acids or MEM non-essential amino acids or glutamine or GlutaMAX™. Said non-essential amino acids or MEM non-essential amino acids may be present in a concentration of about 0.1 mM The neural differentiation medium optionally does not contain exogenously added Noggin. The neural differentiation culture medium optionally does not comprises an exogenously added BMP signaling inhibitor.

Step (a) may comprise (i) culturing eye field progenitor cells until the cells form spheres form, and (ii) plating the spheres under adherent conditions.

Step (i) may comprise culturing the cells on low-adherent plates. Step (i) may comprise culturing the cells in a hanging drop. The culture of step (i) may be formed by mechanically or enzymatically breaking cultured cells into a single cell suspension. Step (i) may be continued for 1-10, 3-8, or about 5 days.

Step (ii) may comprise plating the spheres on Matrigel™. Step (ii) may comprise plating the spheres on laminin or collagen. Step (ii) may be continued until said culture is confluent.

Steps (i) and (ii) may be repeated in an alternating fashion.

Said cells may be cultured in said neural differentiation medium for about 10-60 days or about 15-35 days or about 25 days.

Said retinal neural progenitor cells may differentiate from said eye field progenitor cells and may be present in increasing numbers in said culture.

Said retinal neural progenitor cells may comprise at least 50%, at least 75%, at least 85%, at least 95%, at least 99% or about 100% of the cells in said culture. Said retinal neural progenitor cells may express one or both of the PAX6 and CHX10 markers, and thus may be PAX6 (+) and/or CHX10 (+). Said retinal neural progenitor cells may be SOX2–. Said retinal neural progenitor cells may be Tuj1 (+) or Tuj1 (–).

Said cells may be cultured in said neural differentiation medium for about 10-330 days or about 15-300 days or about 10-100 days or about 15-100 days or about 100 days.

Said photoreceptor progenitor cells differentiate from said retinal neural progenitor cells and may be present in increasing numbers in said culture.

Said photoreceptor progenitor cells may comprise at least 50%, at least 75%, at least 85%, at least 95%, at least 99% or about 100% of the cells in said culture. Said photoreceptor progenitor cells may be PAX6 (+) and/or CHX10 (–). Said photoreceptor progenitor cells may express one or more of the Nr2e3, Trβ2, Mash1, RORB and/or NRL markers, and thus may be Nr2e3 (+), Trβ2 (+), Mash1 (+), RORB (+) and/or NRL (+).

Said cells may be cultured in said neural differentiation medium for at least about 130 days, at least about 160 days, at least about 190 days, or longer, whereby said photoreceptor progenitor cells exhibit decreased or absent ability to differentiate into cones while retaining the ability to form rods.

The method may further comprise differentiating said photoreceptor progenitor cells into photoreceptors.

Said eye field progenitor cells may be differentiated from a pluripotent cell, ES cell, or iPS cell, which pluripotent cell, ES cell, or iPS cell may optionally be human.

In another aspect, said retinal neural progenitor cells may be human.

In another aspect, the disclosure provides a composition comprising retinal neural progenitor cells produced according to any method described herein, e.g., the methods described in the preceding paragraphs. In another aspect, the disclosure provides a composition comprising retinal neural progenitor cells, which are optionally human.

Said retinal neural progenitor cells may comprise at least 50%, at least 75%, at least 85%, at least 95%, at least 99% or about 100% of the cells in said culture.

Said retinal neural progenitor cells may express one or both of the PAX6 and CHX10 markers, and thus may be PAX6 (+) and/or CHX10 (+). Said retinal neural progenitor cells may be SOX2 (–). Said retinal neural progenitor cells may be Tuj1 (+) or Tuj1 (–).

Said retinal neural progenitor cells may be cryopreserved.

In another aspect, the disclosure provides a method of treatment of an individual in need thereof, comprising administering a composition comprising retinal neural progenitor cells, e.g., a composition described herein or a composition produced according to a method described herein, to said individual. Said composition may be administered to the eye, subretinal space, or intravenously. Said photoreceptor progenitor cells may be human.

In another aspect, the disclosure provides a composition comprising photoreceptor progenitor cells produced according to a method described herein, e.g., a method according to the preceding paragraphs. In another aspect, the disclosure provides a composition comprising photoreceptor progenitor cells, which are optionally human.

Said photoreceptor progenitor cells may comprise at least 50%, at least 75%, at least 85%, at least 95%, at least 99% or about 100% of the cells in said culture. Said photoreceptor progenitor cells may be PAX6 (+) and/or CHX10 (–). Said photoreceptor progenitor cells express one or more of the Nr2e3, Trβ2, Mash1, RORβ and/or NRL markers, and thus may be Nr2e3 (+), Trβ2 (+), Mash1 (+), RORβ (+) and/or NRL (+).

Said photoreceptor progenitor cells may be cryopreserved.

In another aspect, the disclosure provides a method of treatment of an individual in need thereof, comprising administering a composition comprising photoreceptor progenitor cells, e.g., a composition as described herein e.g., in the preceding paragraphs, or a composition produced according to the methods described herein e.g., in the preceding paragraphs, to said individual. Said composition may be administered to the eye, subretinal space, or intravenously.

In another aspect, the disclosure provides a method of producing photoreceptor cells, comprising (a) culturing photoreceptor progenitor cells in a photoreceptor differentiation medium.

Said photoreceptor differentiation medium may comprise Neurobasal medium. Said photoreceptor differentiation medium may comprise about 450 mg/ml D-glucose or between about 400 and about 500 mg/ml D-glucose.

The photoreceptor differentiation medium may comprise one or more antibiotics. Said antibiotics may include one or both of penicillin and streptomycin, optionally in concentrations of about 100 unit/ml of penicillin and optionally about 100 μg/ml of streptomycin.

The photoreceptor differentiation medium may comprise N2 supplement. Said N2 supplement may be present in a concentration of about 0.1 to 5% or about 2%.

The photoreceptor differentiation medium may comprise B27 supplement. Said B27 supplement may be present in a concentration of about 0.05-5.0%, about 0.05-2.0% or about 2%.

The photoreceptor differentiation medium may comprise non-essential amino acids or MEM non-essential amino acids or glutamine or GlutaMAX™. Said non-essential amino acids or MEM non-essential amino acids may be present in a concentration of about 0.1 mM Said photoreceptor differentiation medium may comprise forskolin. Said forskolin may be present in the photoreceptor differentiation medium at a concentration between about 1-100 μM or about 5 μM.

Said photoreceptor differentiation medium may comprise BDNF. Said BDNF may be present in the photoreceptor differentiation medium at a concentration between about 1-100 ng/ml or about 10 ng/ml.

Said photoreceptor differentiation medium may comprise CNTF. Said CNTF may be present in the photoreceptor differentiation medium at a concentration between about 1-100 ng/ml or about 10 ng/ml.

Said photoreceptor differentiation medium may comprise LIF. Said LIF may be present in the photoreceptor differentiation medium at a concentration between about 5-50 ng/ml or about 10 ng/ml.

Said photoreceptor differentiation medium may comprise DATP. Said DATP may be present in the photoreceptor differentiation medium at a concentration between about 1-100 μM or about 10 μM.

Said photoreceptor progenitor cells may be differentiated from retinal neural progenitor cells, which are optionally human. Said photoreceptor cells may be human.

In another aspect, the disclosure provides a composition comprising photoreceptor cells produced according to a method as described herein, e.g., in the preceding paragraphs, which are optionally human. Said photoreceptors may be PAX6 (–). Said photoreceptor cells may comprise at least 50%, at least 75%, at least 85%, at least 95%, at least 99% or about 100% of the cells in said culture. Said photoreceptor cells may be cryopreserved.

In another aspect, the disclosure provides a method of treatment of an individual in need thereof, comprising administering a composition comprising photoreceptor cells, e.g., a composition as described herein such as in the preceding paragraphs or a composition produced by a method as described herein e.g., in the preceding paragraphs, to said individual. Said composition may be administered to the eye, subretinal space, or intravenously.

In another embodiment, the invention is directed to a substantially pure preparation of photoreceptor progenitor cells (PRPCs) or photoreceptor cells (PRs) of human origin, preferably non-donor derived photoreceptor progenitor cells or photoreceptor cells, originating from cells not grown on a mouse fibroblast feeder platform. For example, the preparation may be 85%-95% pure. In an embodiment, the invention is directed to a method of preparing the substantially pure preparation of PRPCs or PRs of human origin which omits the need for cells derived from a mouse fibroblast feeder platform. Replacing a feeder system with the methods of the present invention produces a greater homogeneity of photoreceptors cells, e.g., at 75%-100% or 85%-95%. The differentiation of the feeder-free stem cells can also occur in the absence of the introduction of exogenous inducing factors, which is a substantial improvement over the prior art. The optional addition of Noggin, however, can accelerate differentiation of the stem cells, even though it is not necessary for differentiation to occur. The resultant photoreceptor progenitor cells are uniquely characterized immunocytochemically as PAX6 positive and CHX10 negative.

BRIEF DESCRIPTION OF THE DRAWINGS

(FIG. 2A) At day 1 after cell differentiation, cells at the colony margin were column-shaped (arrow). (FIG. 2B) At day 10 after differentiation, the edge cells became big and flat (arrow head) and the central cells were small and compact (arrow). (FIG. 2C) Rosette like structures formed at day 21.

FIGS. 3A-3E: Cells cultured at 21 days after initiation of differentiation expressed eye-field transcription factors. (FIG. 3A) Co-expression of PAX6 and RX1. (FIG. 3B) 93% of cells co-expressed PAX6 and RX1 as shown by dual-color flow cytometric analysis. (FIG. 3C) Cells expressed Nestin. (FIG. 3D) Cells expressed SOX2. In both (C) and (D), DAPI labels cell nuclei. (FIG. 3E) RT-PCR analysis of transcripts of eye field transcription factors: RX1, PAX6, LHX2, SIX3, SIX6, TBX3 and SOX2.

(FIG. 4A) Morphology of cells. After plating on Matrigel™, neurons migrated out from cell aggregates (arrow). A few epithelial-like cells (arrow head) are observed around cell aggregates. (FIG. 4B) Upper panel, phase contrast image of migrating neurons; Lower panel, migrating neurons expressed Tuj1. (FIG. 4C) Cells co-expressed PAX6 and CHX10.

(FIG. 5A) Morphology of cells. (FIG. 5B) Cells express PAX6 but not CHX10. (FIG. 5C) The expression of Recoverin was restricted to the cytoplasm of the cell body. (FIG. 5D) Real-time RT-PCT analysis of transcripts of Rhodopsin, Opsin, and Recoverin in retinal neural progenitors (RNPs) and photoreceptor progenitor cells (indicated as PhRPs).

FIG. 9: Scotopic ERG intensity-response function recorded at one month after systemic cell injection. Stimulus intensity curves for scotopic a-waves (upper panel) and b-waves (lower panel) from ELOVL4-TG2 mice administered PBS, photoreceptor progenitor cells (indicated as PhRPs) or retinoic acid treated photoreceptor progenitor cells (PhRPs-RA). Blank represents untreated mice. #, p<0.01 (vs. PBS).

Figure 10A:
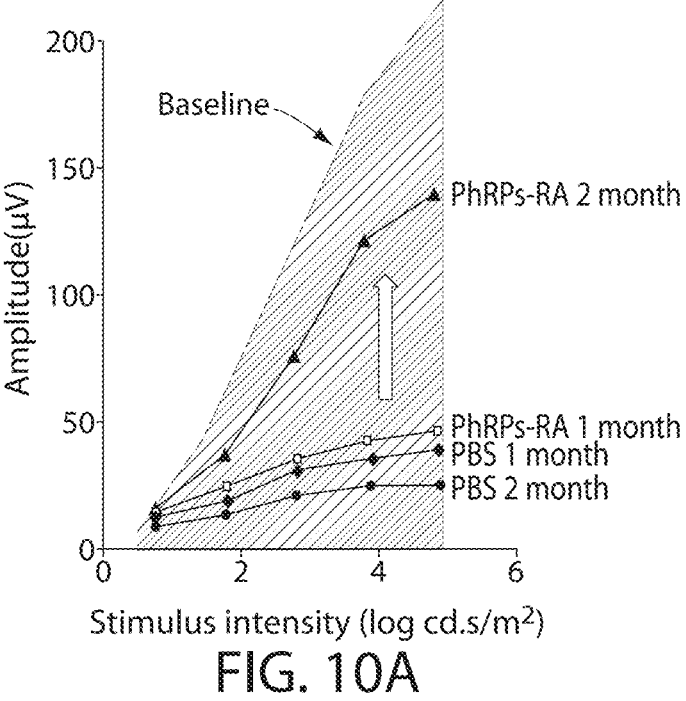
Figure 10B:
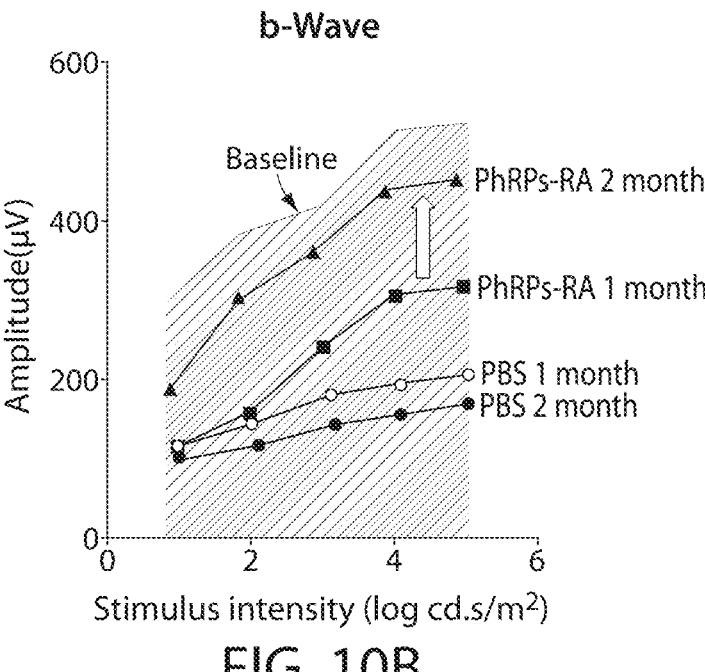

FIGS. 10A-10B. Photoreceptor progenitor cell systemic injection restores rod function between one month and two months after cell transplantation. Scotopic ERG amplitude of a-waves (FIG. 10A) and b-waves (FIG. 10B) at one and two month after cell injection from ELOVL4-TG2 mice administered PBS (PBS) or retinoic acid treated photoreceptor progenitor cells (PhRPs-RA).

Figure 10C:
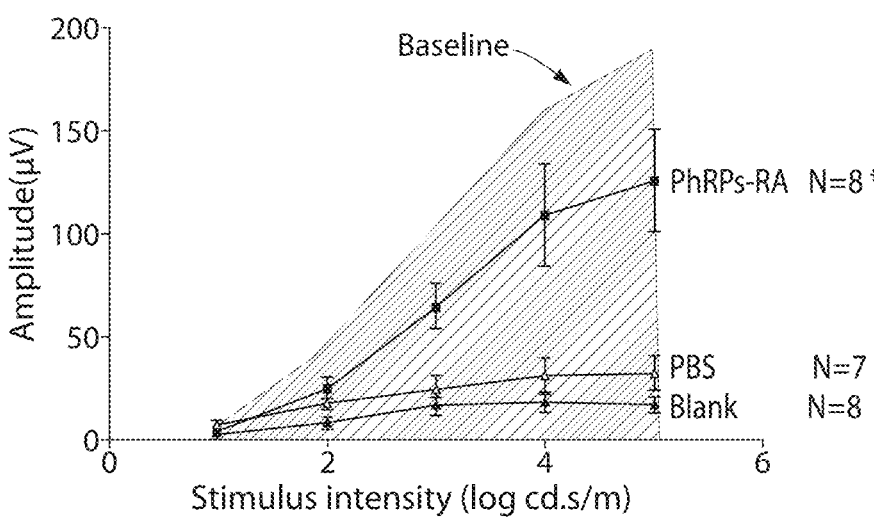
Figure 10C:
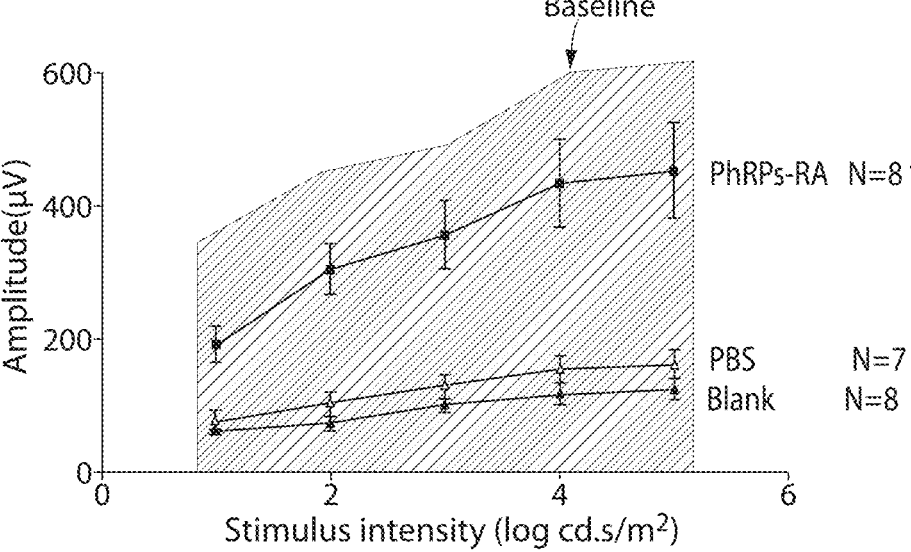

FIG. 10C: Scotopic ERG intensity-response function recorded at two months after systemic cell injection. Stimulus intensity curves for scotopic a-waves (upper panel) and b-waves (lower panel) from ELOVL4-TG2 mice administered PBS or retinoic acid treated photoreceptor progenitor cells (PhRPs-RA). Blank represents untreated mice. Baseline is the level recorded at 4 weeks. *, p<0.001 (vs. PBS).

Figure 11:
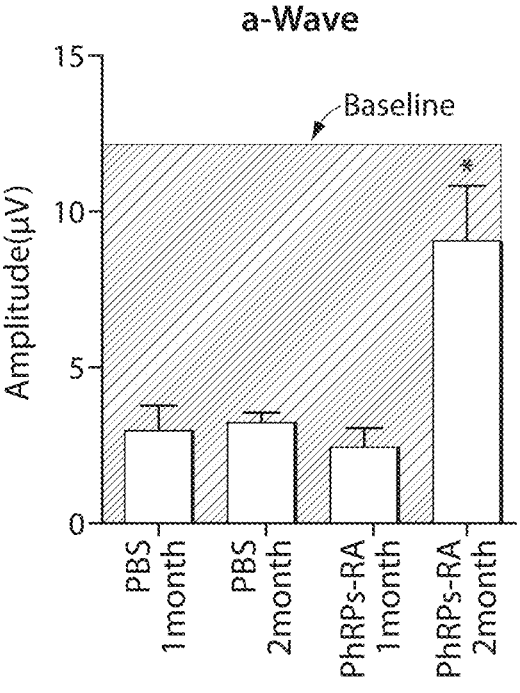
Figure 11:
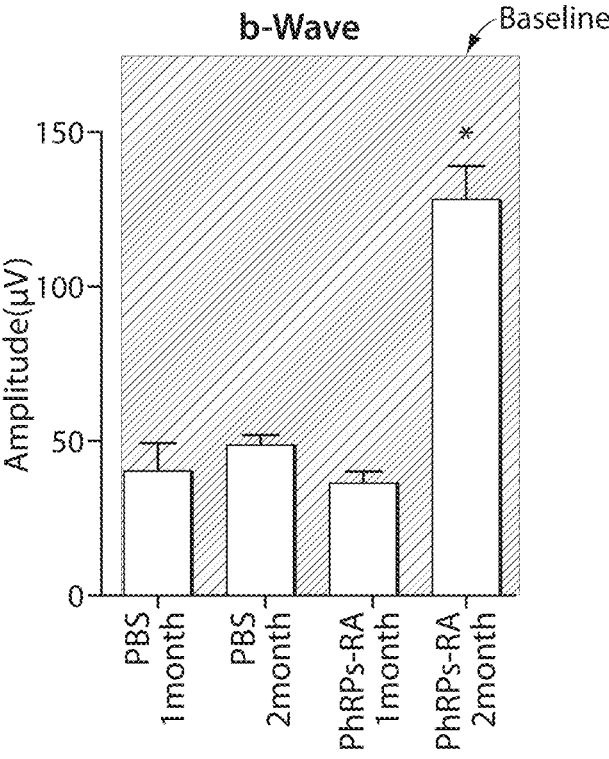

FIG. 11: Photopic ERG amplitude of a-waves (upper panel) and b-waves (lower panel) at one and two month after cell injection from ELOVL4-TG2 mice administered with PBS or retinoic acid treated Photoreceptor progenitors (PhRPs-RA). $, p<0.001 (vs. PBS 2 month).

Figure 12:
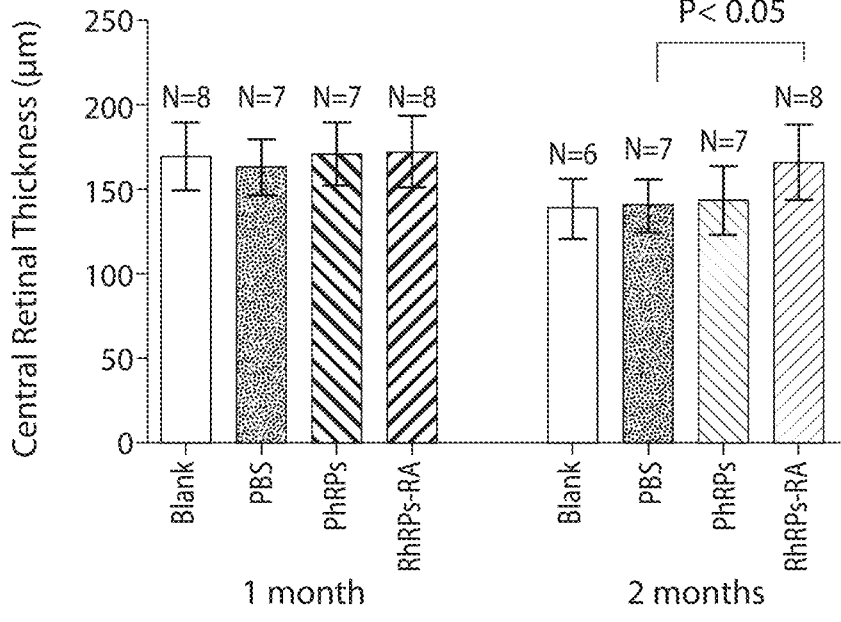

FIG. 12: Whole central retina thickness measured by OCT at one and two months after cell injection from untreated ELOVL4-TG2 mice (blank) and mice administered PBS, photoreceptor progenitor cells (PhRPs), or retinoic acid treated photoreceptor progenitor cells (PhRPs-RA).

Figure 13A:
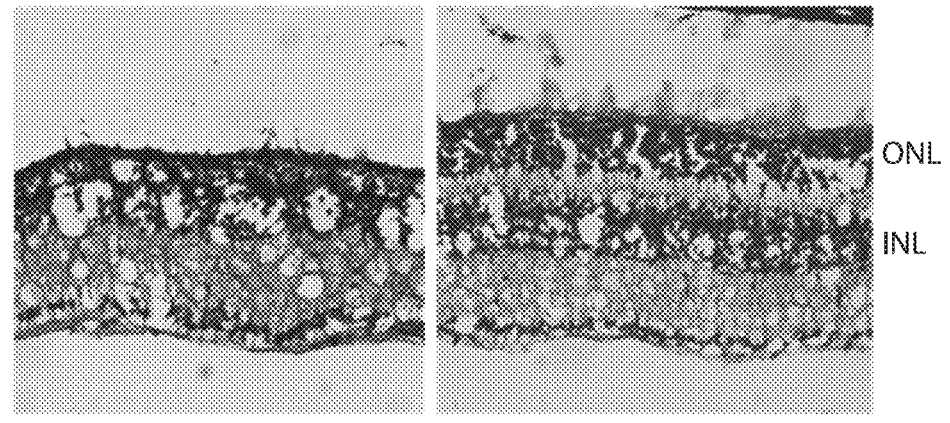
Figure 13B:
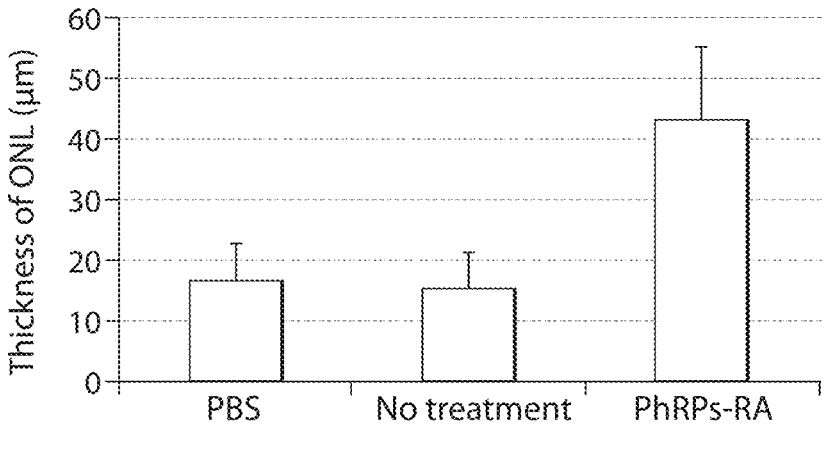

FIGS. 13A-13B: (FIG. 13A) Representative images of retina HE staining at two months after cell injection from ELOVL4-TG2 mice administered PBS (Left panel) and retinoic acid treated photoreceptor progenitor cells (Right panel). ONL, outer nuclear layer. INL, internal nuclear layer. (FIG. 13B), Quantification of the thickness of ONL of retina at two month after cell injection from untreated ELOVL4-TG2 mice (blank) and mice administered PBS or retinoic acid treated Photoreceptor progenitors (PhRPs-RA).

Figure 14:
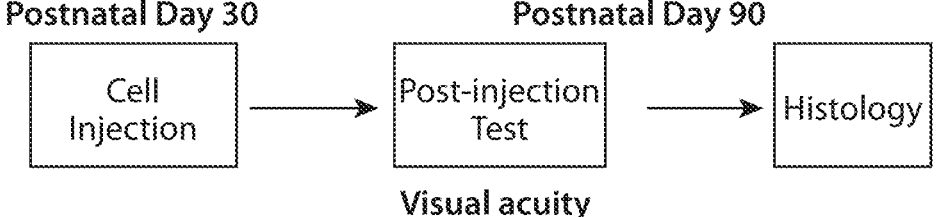

FIG. 14: Schematic diagram of animal studies in RCS rats.

Figure 15A:
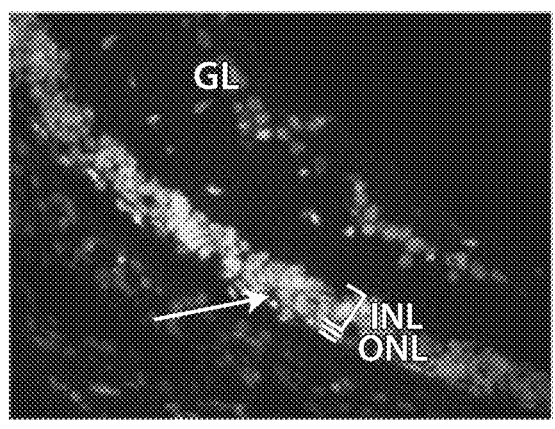
Figure 15B:
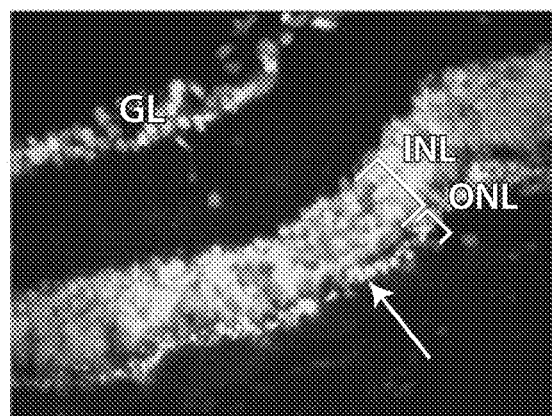
Figure 15C:
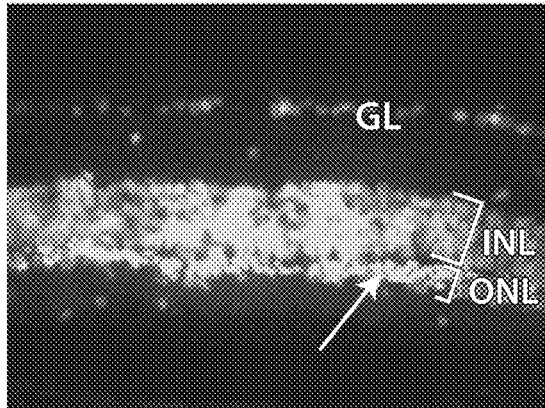

FIGS. 15A-15C: Preservation of host photoreceptor cells after transplantation of human ES cell-derived photoreceptor progenitor cells. Retinal sections at P90 stained with DAPI: (FIG. 15A) Outer nuclear layer (ONL) is reduced to 0-1 layer in control rats. (FIG. 15B) Rescued ONL cells in RCS rat after intravenous cell injection, which is 2-4 cells deep. (FIG. 15C) Rescued ONL cells in RCS rat receiving intravitreal cell injection, which is 3-5 cells deep. INL, inner nuclear layer; GL, ganglion cell layer.

Figure 16A:
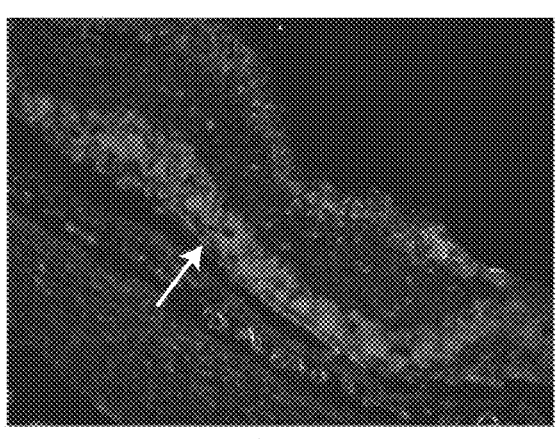
Figure 16B:
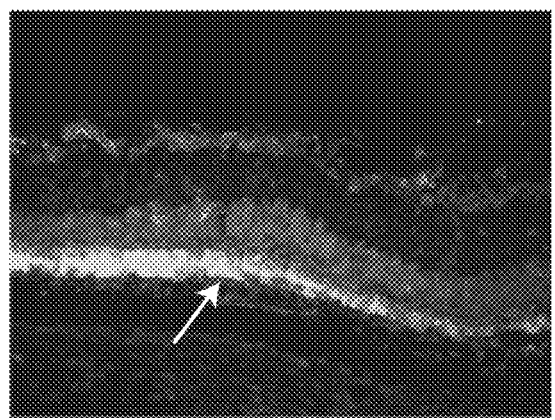
Figure 16C:
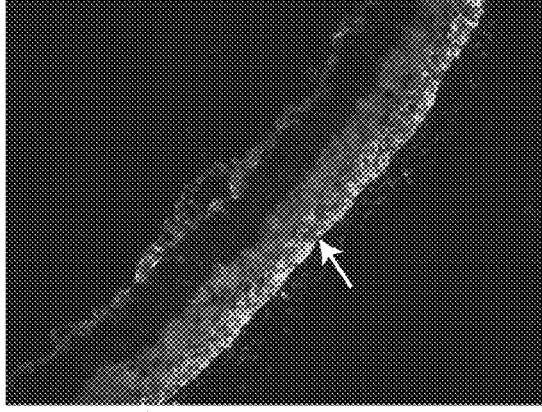

FIGS. 16A-16C: Preservation of host rod photoreceptor cell outer segment (OS) after transplantation of human ES cell-derived photoreceptor progenitor cells. Retinal sections at P90 stained for Rhodopsin. (FIG. 16A) Complete loss of rod OS in control rats (arrow). (FIG. 16B) Expression of Rhodopsin in the OS of host rod photoreceptor cells in RCS rat retina after intravenous injection of photoreceptor progenitor cells (arrow). (FIG. 16C) Expression of Rhodopsin in the OS of host rod photoreceptor cells in RCS rat retina after intravitreal transplantation of photoreceptor progenitor cells (arrow).

Figure 17A:
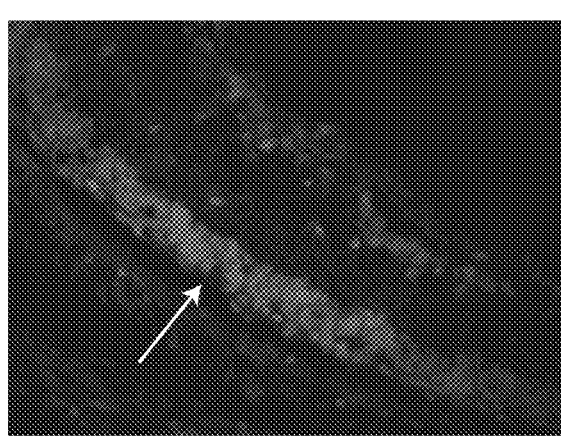
Figure 17B:
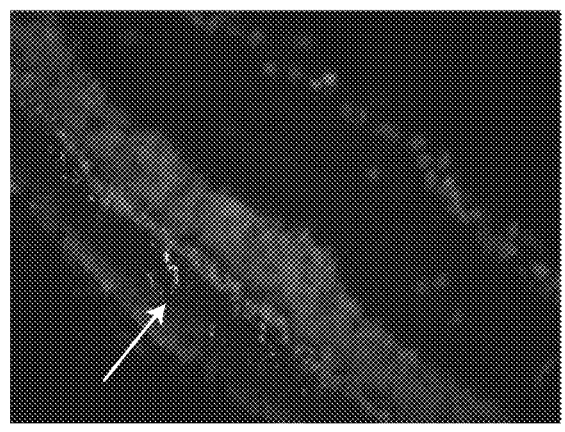
Figure 17C:
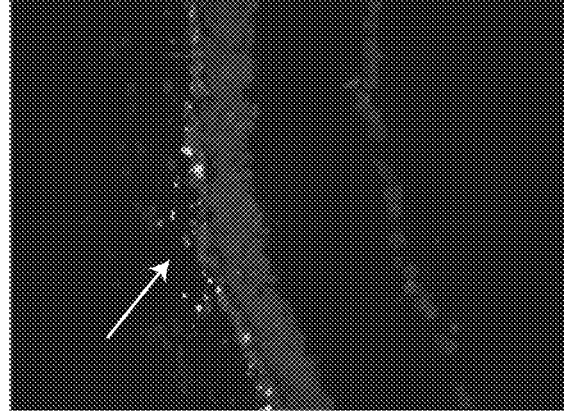

FIGS. 17A-17C: Preservation of host cone photoreceptor cell outer segment (OS) after transplantation of human ES cell-derived photoreceptor progenitor cells. Retinal sections at P90 stained for Opsin. (FIG. 17A) Complete loss of cone OS in control rats. (FIG. 17B) Expression of Opsin in the OS of host cone photoreceptor cells in RCS rat retina after intravenous injection of photoreceptor progenitor cells (arrow). (FIG. 17C) Expression of Opsin in the OS of host cone photoreceptor cells in RCS rat retina after intravitreal transplantation of photoreceptor progenitors (arrow).

Figure 18A:
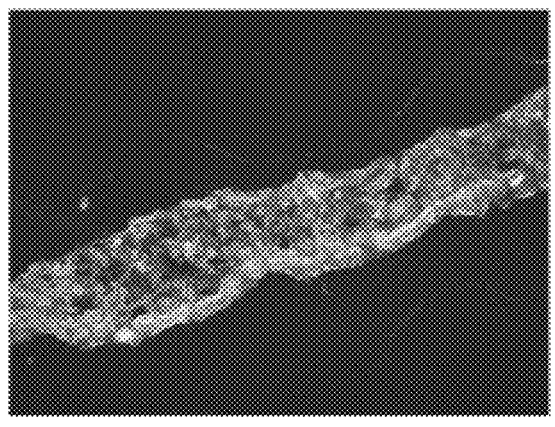
Figure 18B:
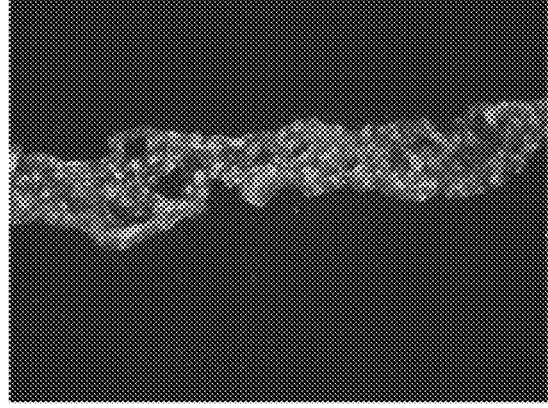

FIGS. 18A-18B: Human ES cell-derived photoreceptor progenitor cells transplanted into the vitreous of RCS rats differentiated into mature rod photoreceptor cells. Retinal sections at P90 stained for rhodopsin (FIG. 18A), Recoverin (FIG. 18B). Human cells were labeled with anti-HuNU antibody. DAPI labeled all nuclei.

Figure 19:
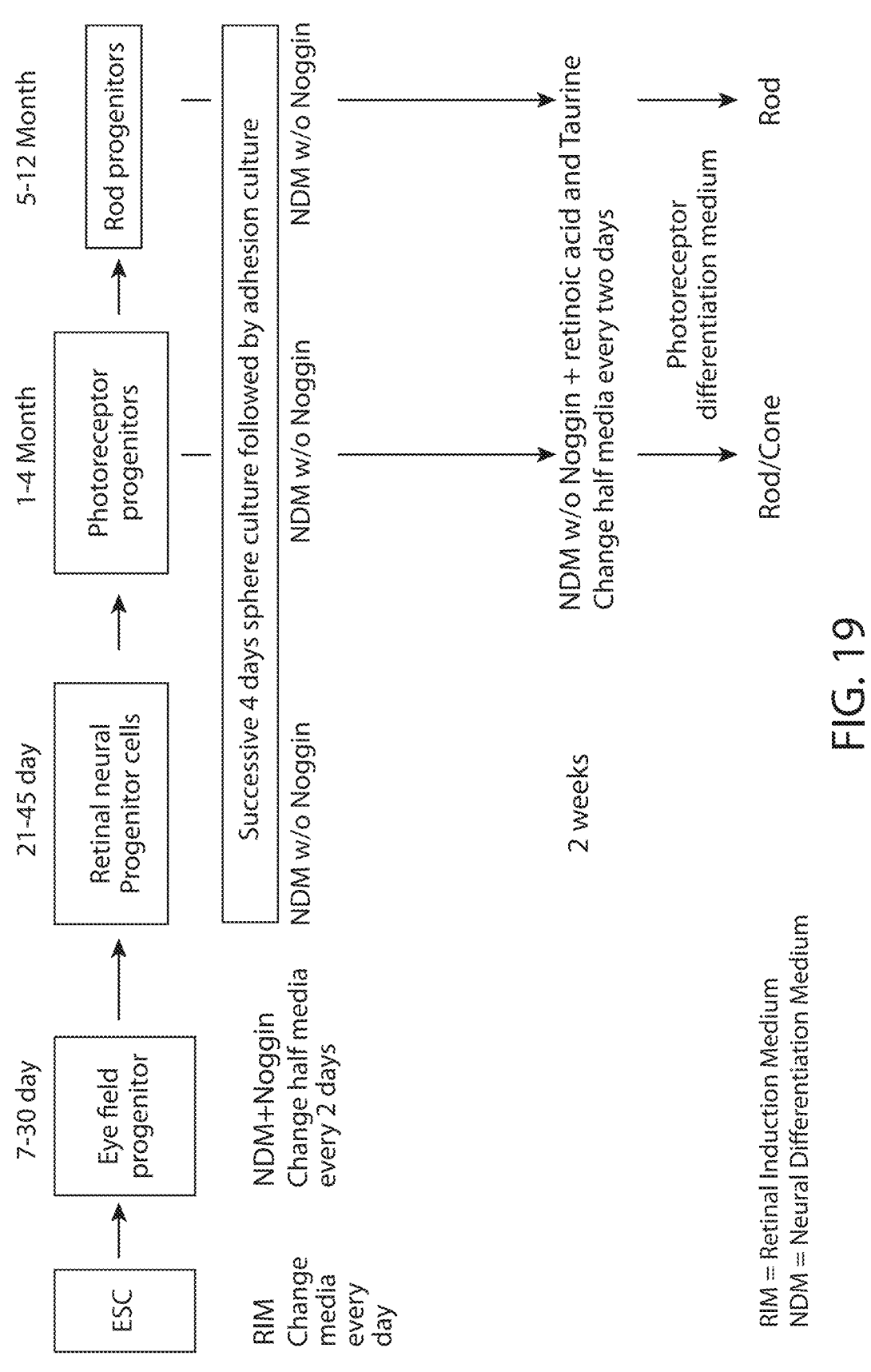

FIG. 19: Illustrates the overall method used for photoreceptor development in Examples 1-2 and further illustrates the media used at each step of the process.

Figure 20:
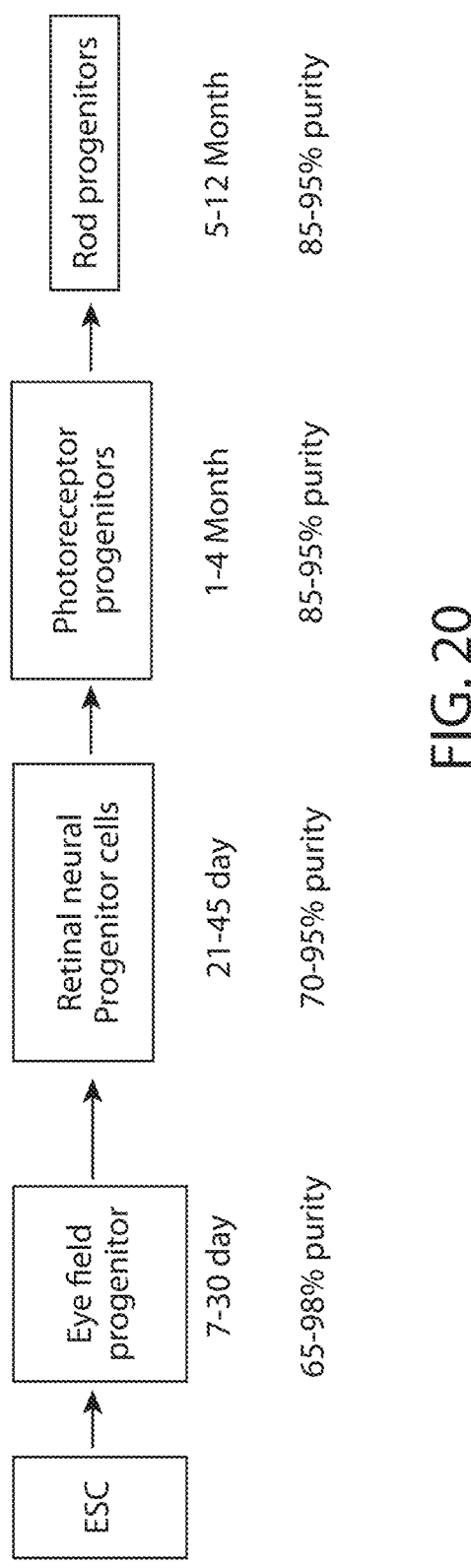

FIG. 20: Illustrates the timing of photoreceptor cell and photoreceptor progenitor cell development in Examples 1-2.

FIGS. 21A-21E: Show the components of culture media and media supplements used in the Examples.

Figure 22:
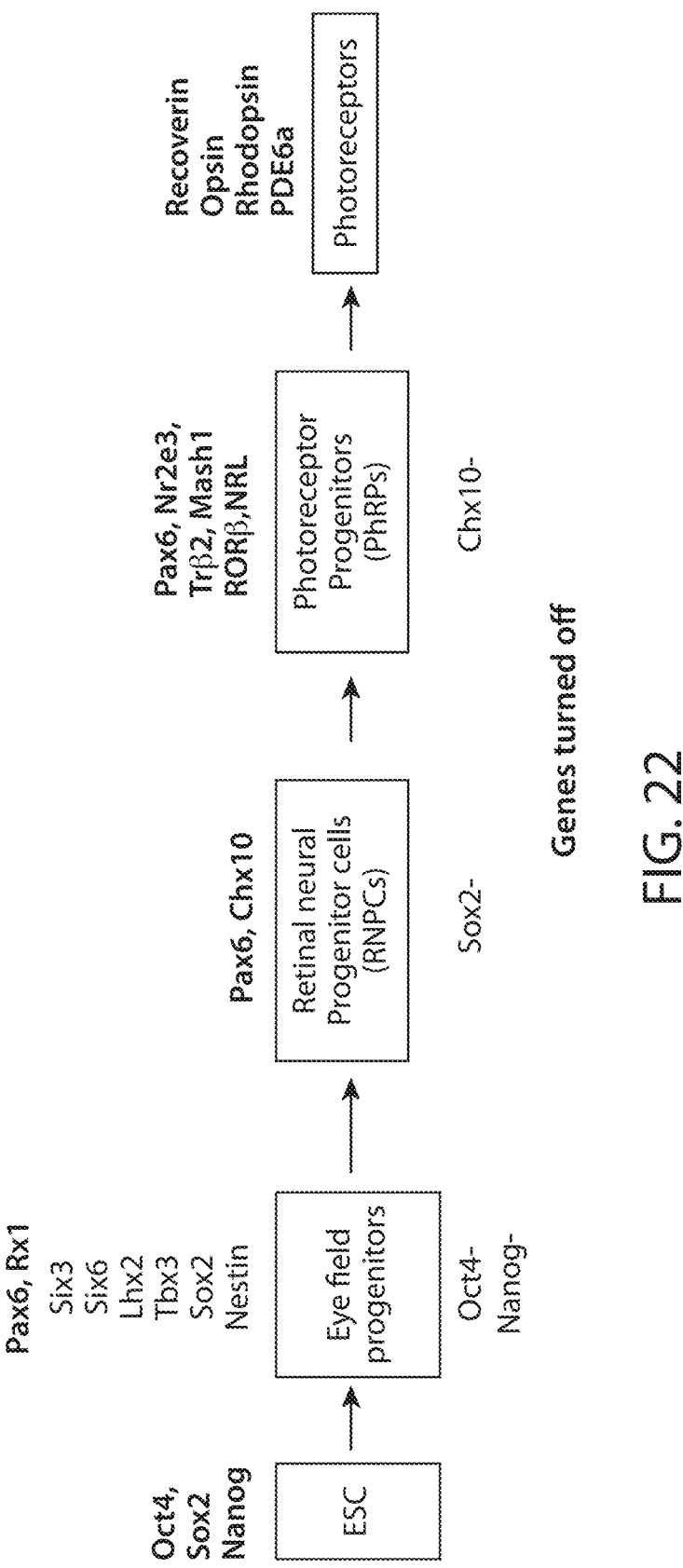

FIG. 22: Illustrates the gene expression pattern of ESC, eye field progenitor cells, retinal neural progenitor cells, photoreceptor progenitor cells, and photoreceptor cells during in vitro differentiation from human pluripotent stem cells.

DETAILED DESCRIPTION

Definitions: As defined here, singular forms are provided for illustrative purposes, but may also apply to plural versions of the phrase. The following definitions are meant to supplement conventional definitions of the terms as they would be understood by persons of ordinary skill.

"Substantially pure preparation of photoreceptor progenitor cells (PRPCs)." As used herein, this phrase refers to a preparation of cells (e.g., a composition comprising cells) wherein the cells are at least 75% pure or preferably at least 85% pure, at least 95% pure, or are about 85% to 95% pure. For example, the level of purity may be quantified by determining the proportion of cells in the preparation that express one or more markers, such as those markers of PRPCs (including those markers identified in this application or others known in the art), relative to the total number of cells in the preparation, e.g., by detecting cells that do or do not express said one or more markers. Optionally expression of markers indicative of non-PRPC cells may also be detected, thereby facilitating detection and/or quantitation of said cells. Exemplary methods that may be utilized to include, without limitation, Fluorescence Activated Cell Sorting (FACS), immunohistochemistry, in situ hybridization, and other suitable methods known in the art. Optionally the determination of purity may be performed disregarding non-viable cells present in the preparation.

"Substantially pure preparation of photoreceptor cells (PRs) of human origin." As used herein, this phrase refers to a preparation of cells (e.g., a composition comprising cells) wherein the cells are at least 75% pure or preferably at least 85% pure, at least 95% pure, or are about 85% to 95% pure. For example, the level of purity may be quantified by determining the proportion of cells in the preparation that express one or more markers, such as those markers of PRs (including those markers identified in this application or others known in the art), relative to the total number of cells in the preparation, e.g., by detecting cells that do or do not express said one or more markers. Optionally expression of markers indicative of non-PR cells may also be detected, thereby facilitating detection and/or quantitation of said cells. Exemplary methods that may be utilized to include, without limitation, Fluorescence Activated Cell Sorting (FACS), immunohistochemistry, in situ hybridization, and other suitable methods known in the art. Optionally the determination of purity may be performed disregarding non-viable cells present in the preparation.

"Embryoid bodies" refers to clumps or clusters of pluripotent cells (e.g., iPSC or ESC) which may be formed by culturing pluripotent cells under non-attached conditions, e.g., on a low-adherent substrate or in a "hanging drop." In these cultures, pluripotent cells can form clumps or clusters of cells denominated as embryoid bodies. See Itskovitz-Eldor et al., Mol Med. 2000 Feb.; 6 (2): 88-95, which is hereby incorporated by reference in its entirety. Typically, embryoid bodies initially form as solid clumps or clusters of pluripotent cells, and over time some of the embryoid bodies come to include fluid filled cavities, the latter former being referred to in the literature as "simple" EBs and the latter as "cystic" embryoid bodies.

The term "embryonic stem cell" (ES cell or ESC) is used herein as it is used in the art. This term includes cells derived from the inner cell mass of human blastocysts or morulae, including those that have been serially passaged as cell lines. The ES cells may be derived from fertilization of an egg cell with sperm, as well as using DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, androgenesis, or the reprogramming of chromatin and subsequent incorporation of the reprogrammed chromatin into a plasma membrane to produce a cell. Embryonic stem cells, regardless of their source or the particular method used to produce them, can be identified based on (i) the ability to differentiate into cells of all three germ layers, (ii) expression of at least OCT4 and alkaline phosphatase, and (iii) ability to produce teratomas when transplanted into immunodeficient animals. Embryonic stem cells that may be used in embodiments of the present invention include, but are not limited to, human ES cells ("ESC" or "hES cells") such as MA01, MA09, ACT-4, No. 3, H1, H7, H9, H14 and ACT30 embryonic stem cells. Additional exemplary cell lines include NED1, NED2, NED3, NED4, NED5, and NED7. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." Nature 444:481-485. The human ES cells used in accordance with exemplary embodiments of the present invention may be derived and maintained in accordance with GMP standards.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that are: (a) capable of inducing teratomas when transplanted in immunodeficient (SCID) mice; (b) capable of differentiating to cell types of all three germ layers (e.g., can differentiate to ectodermal, mesodermal, and endodermal cell types); and (c) express one or more markers of embryonic stem cells (e.g., express OCT4, alkaline phosphatase. SSEA-3 surface antigen, SSEA-4 surface antigen, NANOG, TRA-1-60, TRA-1-81, SOX2, REX1, etc). In certain embodiments, pluripotent stem cells express one or more markers selected from the group consisting of: OCT4, alkaline phosphatase, SSEA-3, SSEA-4, TRA-1-60, and TRA-1-81. Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPSCs) generated by reprogramming a somatic cell by expressing a combination of factors (herein referred to as reprogramming factors). The iPSCs can be generated using fetal, postnatal, newborn, juvenile, or adult somatic cells.

In certain embodiments, factors that can be used to reprogram somatic cells to pluripotent stem cells include, for example, a combination of OCT4 (sometimes referred to as OCT3/4), SOX2, c-Myc, and Klf4. In other embodiments, factors that can be used to reprogram somatic cells to pluripotent stem cells include, for example, a combination of OCT4, SOX2, NANOG, and LIN28. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell. In other embodiments, additional reprogramming factors are identified and used alone or in combination with one or more known reprogramming factors to reprogram a somatic cell to a pluripotent stem cell. Induced pluripotent stem cells are defined functionally and include cells that are reprogrammed using any of a variety of methods (integrative vectors, non-integrative vectors, chemical means, etc). Pluripotent stem cells may be genetically modified or otherwise modified to increase longevity, potency, homing, to prevent or reduce alloimmune responses or to deliver a desired factor in cells that are differentiated from such pluripotent cells (for example, photoreceptors, photoreceptor progenitor cells, rods, cones, etc. and other cell types described herein, e.g., in the examples).

"Induced pluripotent stem cells" (iPS cells or iPSC) can be produced by protein transduction of reprogramming factors in a somatic cell. In certain embodiments, at least two reprogramming proteins are transduced into a somatic cell to successfully reprogram the somatic cell. In other embodiments, at least three reprogramming proteins are transduced into a somatic cell to successfully reprogram the somatic cell. In other embodiments, at least four reprogramming proteins are transduced into a somatic cell to successfully reprogram the somatic cell.

The pluripotent stem cells can be from any species. Embryonic stem cells have been successfully derived in, for example, mice, multiple species of non-human primates, and humans, and embryonic stem-like cells have been generated from numerous additional species. Thus, one of skill in the art can generate embryonic stem cells and embryo-derived stem cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, gerbils, squirrel, guinea pig, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Similarly, iPS cells can be from any species. These iPS cells have been successfully generated using mouse and human cells. Furthermore, iPS cells have been successfully generated using embryonic, fetal, newborn, and adult tissue. Accordingly, one can readily generate iPS cells using a donor cell from any species. Thus, one can generate iPS cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Induced pluripotent stem cells can be generated using, as a starting point, virtually any somatic cell of any developmental stage. For example, the cell can be from an embryo, fetus, neonate, juvenile, or adult donor. Exemplary somatic cells that can be used include fibroblasts, such as dermal fibroblasts obtained by a skin sample or biopsy, synoviocytes from synovial tissue, foreskin cells, cheek cells, or lung fibroblasts. Although skin and cheek provide a readily available and easily attainable source of appropriate cells, virtually any cell can be used. In certain embodiments, the somatic cell is not a fibroblast.

The induced pluripotent stem cell may be produced by expressing or inducing the expression of one or more reprogramming factors in a somatic cell. The somatic cell may be a fibroblast, such as a dermal fibroblast, synovial fibroblast, or lung fibroblast, or a non-fibroblastic somatic cell. The somatic cell may be reprogrammed through causing expression of (such as through viral transduction, integrating or non-integrating vectors, etc.) and/or contact with (e.g., using protein transduction domains, electroporation, microinjection, cationic amphiphiles, fusion with lipid bilayers containing, detergent permeabilization, etc.) at least 1, 2, 3, 4, 5 reprogramming factors. The reprogramming factors may be selected from OCT3/4, SOX2, NANOG, LIN28, C-MYC, and KLF4. Expression of the reprogramming factors may be induced by contacting the somatic cells with at least one agent, such as a small organic molecule agents, that induce expression of reprogramming factors.

Further exemplary pluripotent stem cells include induced pluripotent stem cells generated by reprogramming a somatic cell by expressing or inducing expression of a combination of factors ("reprogramming factors"). iPS cells may be obtained from a cell bank. The making of iPS cells may be an initial step in the production of differentiated cells. iPS cells may be specifically generated using material from a particular patient or matched donor with the goal of generating tissue-matched PHRPS or photoreceptor cells. iPSCs can be produced from cells that are not substantially immunogenic in an intended recipient, e.g., produced from autologous cells or from cells histocompatible to an intended recipient.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. See, e.g., Yu et al., Science. 2009 May 8; 324 (5928): 797-801, which is hereby incorporated by reference in its entirety. When reprogramming factors are expressed using non-integrative vectors, the factors may be expressed in the cells using electroporation, transfection, or transformation of the somatic cells with the vectors. For example, in mouse cells, expression of four factors (OCT3/4, SOX2, C-MYC, and KLF4) using integrative viral vectors is sufficient to reprogram a somatic cell. In human cells, expression of four factors (OCT3/4, SOX2, NANOG, and LIN28) using integrative viral vectors is sufficient to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells.

To confirm the pluripotency of the iPS cells, the cells may be tested in one or more assays of pluripotency. For example, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPSC is obtained it may be used to produce cell types disclosed herein, e.g., photoreceptor progenitor cells, photoreceptor cells, rods, cones, etc. and other cell types described herein, e.g., in the examples.

"Stem cell" is used here to refer to a pluripotent cell which can proliferate and/or differentiate into a mature cell and is optionally of human origin.

"Adult stem cell" refers to a multipotent cell isolated from adult tissue and can include bone marrow stem cells, cord blood stem cells and adipose stem cells and is of human origin.

"Retina" refers to the neural cells of the eye, which are layered into three nuclear layers comprised of photoreceptors, horizontal cells, bipolar cells, amacrine cells, Müller glial cells and ganglion cells.

"Progenitor cell" refers to a cell that remains mitotic and can produce more progenitor cells or precursor cells or can differentiate to an end fate cell lineage.

"Precursor cell" refers to a cell capable of differentiating to an end fate cell lineage. In embodiments of the invention, an "eye field progenitor cell" is differentiated from embryonic stem cells or induced pluripotent stem cells and expresses the markers PAX6 and RX1RX1. In embodiments of the invention, a "retinal neural progenitor cell" refers to a cell differentiated from embryonic stem cells or induced pluripotent stem cells, that expresses the cell markers PAX6 and CHX10. In embodiments of the invention, "photoreceptor progenitor" refers to cells differentiated from embryonic stem cells or induced pluripotent stem cells and that expresses the marker PAX6 while not expressing the marker CHX10 (i.e. CHX10 (–)). These cells transiently express CHX10 at retinal neural progenitor stage, but the CHX10 expression is turned off when cells differentiate into the photoreceptor progenitor stage. Also, "photoreceptor" may refer to post-mitotic cells differentiated from embryonic stem cells or induced pluripotent stem cells and that expresses the cell marker rhodopsin or any of the three cone opsins, and optionally express the rod or cone cGMP phosphodiesterase. The photoreceptors may also express the marker recoverin, which is found in photoreceptors. The photoreceptors may be rod and/or cone photoreceptors.

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Therapy," "therapeutic," "treating," "treat" or "treatment", as used herein, refers broadly to treating a disease, arresting or reducing the development of the disease or its clinical symptoms, and/or relieving the disease, causing regression of the disease or its clinical symptoms. Therapy encompasses prophylaxis, prevention, treatment, cure, remedy, reduction, alleviation, and/or providing relief from a disease, signs, and/or symptoms of a disease. Therapy encompasses an alleviation of signs and/or symptoms in patients with ongoing disease signs and/or symptoms. Therapy also encompasses "prophylaxis" and "prevention". Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms. Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms.

Cell Markers: Exemplary cell markers that may be assessed for expression include the following: PAX6, RX1, SIX3, SIX6, LHX2, TBX3, SOX2, CHX10, Nestin, TRbeta2, NR2E3, NRL, MASH1, RORB, Recoverin, Opsin, Rhodopsin, rod and cone cGMP Phosphodiesterase, which may be assessed at the protein and/or mRNA (see Fischer A J, Reh T A, Dev Neurosci. 2001; 23 (4-5): 268-76; Baumer et al., Development. 2003 Jul.; 130 (13): 2903-15, Swaroop et al., Nat Rev Neurosci. 2010 Aug.; 11 (8): 563-76, Agathocleous and Harris, Annu. Rev. Cell Dev. Biol. 2009. 25:45-69, each of which is hereby incorporated by reference in its entirety). Said marker identifiers are generally used as in the literature and in the art, particular in the fields of art in related to the contexts in which those gene identifiers are recited herein, which may include literature related to photoreceptors, rods, cones, photoreceptor differentiation, photoreceptor progenitors, neural differentiation, neural stem cells, pluripotent stem cells, and other fields as indicated by context. Additionally, the markers are generally human, e.g., except where the context indicates otherwise. The cell markers can be identified using conventional immunocytochemical methods or conventional PCR methods which techniques are well known to those of ordinary skill in the art.

Cell Culture Media: In embodiments of the invention, the cells are stored, proliferated or differentiated in various cell culture media. Retinal induction medium is utilized for the stem cell production into Eye Field Progenitor Cells. The retinal induction medium may comprise D-glucose, penicillin, streptomycin, N2 supplement (e.g. 0.1-5%), B27 supplement (e.g., 0.005 to 0.2%), MEM Non-essential amino acids solution and optionally including insulin and/or Noggin, and may be in a DMEM/F12 (Invitrogen) or similar base medium. For example, the Retinal induction medium may include at least insulin. Additionally, the insulin concentration may be varied or increased which may promote cell survival and/or yield of differentiated cells. For example, the insulin concentration may be varied across a range and survival and/or differentiation monitored in order to identify an insulin concentration with improves either or both of these attributes. The addition of Noggin is believed not to be necessary but was observed to increase the expression of eye field transcription factors.

Noggin is a secreted BMP inhibitor that reportedly binds BMP2, BMP4, and BMP7 with high affinity to block TGFβ family activity. SB431542 is a small molecule that reportedly inhibits TGFβ/Activin/Nodal by blocking phosphorylation of ACTRIB, TGFβR1, and ACTRIC receptors. SB431542 is thought to destabilize the Activin- and Nanog-mediated pluripotency network as well as suppress BMP induced trophoblast, mesoderm, and endodermal cell fates by blocking endogenous Activin and BMP signals. It is expected that agents having one or more of the aforementioned activities could replace or augment the functions of one or both of Noggin and SB431542, e.g., as they are used in the context of the disclosed methods. For example, applicants envision that the protein Noggin and/or the small molecule SB4312542 could be replaced or augmented by one or more inhibitors that affect any or all of the following three target areas: 1) preventing the binding of the ligand to the receptor; 2) blocking activation of receptor (e.g., dorsomorphin), and 3) inhibition of SMAD intracellular proteins/transcription factors. Exemplary potentially suitable factors include the natural secreted BMP inhibitors Chordin (which blocks BMP4) and Follistatin (which blocks Activin), as well as analogs or mimetics thereof. Additional exemplary factors that may mimic the effect of Noggin include use of dominant negative receptors or blocking antibodies that would sequester BMP2, BMP4, and/or BMP7. Additionally, with respect to blocking receptor phosphorylation, dorsomorphin (or Compound C) has been reported to have similar effects on stem cells. Inhibition of SMAD proteins may also be effected using soluble inhibitors such SIS3 (6,7-Dimethoxy-2-((2E)-3-(1-methyl-2-phenyl-1H-pyrrolo[2,3-b] pyridin-3-yl-prop-2-enoyl))-1,2,3,4-tetrahydroisoquinoline, Specific Inhibitor of Smad3, SIS3), overexpression of one or more of the inhibitor SMADs (e.g., SMAD6, SMAD7, SMAD10) or RNAi for one of the receptor SMADs (SMAD1, SMAD2, SMAD3, SMAD5, SMAD8/9). Another combination of factors expected to be suitable for generating neural progenitors comprises a cocktail of Leukemia Inhibitory Factor (LIF), GSK3 inhibitor (CHIR 99021), Compound E (y secretase inhibitor XXI) and the TGFβ inhibitor SB431542 which has been previously shown to be efficacious for generating neural crest stem cells (Li et al., Proc Natl Acad Sci USA. 2011 May 17; 108 (20): 8299-304). Additional exemplary factors may include derivatives of SB431542, e.g., molecules that include one or more added or different substituents, analogous functional groups, etc. and that have a similar inhibitory effect on one or more SMAD proteins. Suitable factors or combinations of factors may be identified, for example, by contacting pluripotent cells with said factor(s) and monitoring for adoption of eye field progenitor cell phenotypes, such as characteristic gene expression (including expression of the markers described herein, expression of a reporter gene coupled to an eye field progenitor cell promoter, or the like) or the ability to form a cell type disclosed herein such as retinal neural progenitor cells, photoreceptor progenitors, rod progenitors, cones, and/or rods.

Preferably the cells are treated with or cultured in a retinal induction medium prior to culture with a neural differentiation medium. A neural differentiation medium is utilized for Eye Field Progenitor Cell production into Retinal Neural Progenitor Cells. The neural differentiation medium may comprise D-glucose, penicillin, streptomycin, GlutaMAX™, N2 supplement, B27 supplement, MEM Non-essential amino acids solution and optionally including Noggin. The neural differentiation medium may also be utilized for Retinal Neural Progenitor Cell production into Photoreceptor Progenitor Cells but without the inclusion of Noggin. The use of a neural differentiation medium, optionally supplemented with retinoic acid and taurine, followed by utilization of a photoreceptor differentiation medium (Invitrogen) which optionally may comprise D-glucose, penicillin, streptomycin, GlutaMAX™, N2 supplement, B27 supplement with the addition of Forskolin, BDNF, CNTF, LIF and DATP is utilized for Photoreceptor Progenitor Cells production into Photoreceptor Cells. For example the photoreceptor differentiation medium may comprise thyroid hormone, e.g., in an amount that is present in the foregoing medium, or in a different or greater amount. For example said medium may comprise exogenously added thyroid hormone. In exemplary embodiments the photoreceptor differentiation medium may comprise one, two, or all three BDNF, CNTF and DATP, e.g., BDNF, CNTF, DATP, BDNF and CNTF, CNTF and DATP, BDNF and DATP, or all three of BDNF, CNTF and DATP, which medium may optionally comprise Neurobasal Medium and/or may optionally comprise thyroid hormone.

The neural differentiation medium constituents are as follows:

N2: 1% (1 ml of N2/100 ml)

B27: 2% (2 ml of b27/100 ml)

Noggin: 50 ng/ml

Noggin is not needed after cells have all become eye field progenitors.

Embryonic Stem Cells (ESCs) or Adult Stem Cells or Induced Pluripotent Stem Cells (iPS): The ESCs, or Adult Stem Cells or iPS cells utilized herein may be propagated on a feeder-free system, such as in Matrigel™ (a soluble preparation from Engelbreth-Holm-Swarm (EHS) mouse sarcoma cells) or another matrix. Additionally, or alternatively, said pluripotent cells may be cultured on a matrix which may be selected from the group consisting of laminin, fibronectin, vitronectin, proteoglycan, entactin, collagen, collagen I, collagen IV, collagen VIII, heparan sulfate, Matrigel™ (a soluble preparation from Engelbreth-Holm-Swarm (EHS) mouse sarcoma cells), CellStart, a human basement membrane extract, and any combination thereof. Said matrix may comprise, consist of, or consist essentially of Matrigel™ (a soluble preparation from Engelbreth-Holm-Swarm (EHS) mouse sarcoma cells). The stem cells do not form embryoid bodies in culture, which is an improvement over the prior art. The cells differentiate into eye field progenitor cells in the absence of exogenous factors. In an embodiment, ESCs differentiate into eye field progenitor cells in the presence of Noggin.

Eye Field Progenitor Cells (EFPCs): The EFPCs differentiate from ESCs, Adult stem cells or induced pluripotent cells (iPCs) into cells that are PAX6 (+) and RX1 (+). The EFPCs can also be SIX3 (+), SIX6 (+), LHX2 (+), TBX3 (+) Nestin (+) and/or SOX2 (+) and OCT4 (−) and Nanog (−). The differentiation into EFPCs occurs in a retinal induction medium which may comprise DMEM/F12, D-glucose, penicillin, streptomycin, N2 supplement, B27 supplement, MEM non-essential amino acid and insulin. On day 5, when cells reach confluence, cells are changed to neural differentiation medium. Preferably the step of producing EFPCs is performed prior to culturing pluripotent cells in the neural differentiation medium described below, as it has been observed that such culture conditions may adversely affect pluripotent cell viability.

Retinal Neural Progenitor Cells (RNPCs): The RNPCs differentiate from the EFPCs in the absence of exogenous factors. The RNPCs are PAX6 (+) and CHX10 (+). The cells at this state may be Tuj1+ or Tuj1−. Optionally the method may include enriching or purifying Tuj1+ or Tuj1-cells at this stage, and/or purifying or removing strongly Tuj1+ cells and/or purifying or removing strongly Tuj1-cells (e.g., cells lacking even low level detectable expression thereof) and proceeding with the subsequent method steps with one or the other of these populations. In an embodiment, Noggin is added to accelerate the differentiation from EFPCs to RNPCs The differentiation into RNPCs occurs in a neural differentiation media which may comprise Neurobasal Medium (Invitrogen), D-glucose, penicillin, streptomycin, GlutaMAX™, N2 supplement, B27 supplement and MEM non-essential amino acid solution. Noggin may be added at a final concentration of 5-100 µg/ml.

Photoreceptor Progenitor Cells (PhRPCs): The PhRPCs may be differentiated from the RNPCs in the absence of Noggin and in neural differentiation medium). The PRPCs are PAX6 (+) and CHX10 (−). In embodiment, 60%, 70%, 80%, 85%, 90%, or 95% of the PRPCs are PAX6 (+) and CHX10 (−) The PRPCs can also be Nr2e3 (+), Trβ2 (+), Mash1 (+), RORβ (+) and/or NRL (+). The presence of CHX10 would suggest a bipolar cell lineage, but in the present method, the PRPCs have differentiated to a photo-receptor lineage, and therefore do not possess CHX10 at this stage. The cells may be grown as spheres or neurospheres (e.g., on low attachment plates or optionally on hanging drop cultures, in a low-gravity environment, or other suitable culture condition).

Photoreceptors (PRs): The PRs may differentiate from the PhRPCs in a two-step differentiation process 1) Adding neural differentiation medium with retinoic acid and taurine for 2 weeks and 2) addition of the photoreceptor differen-tiation medium.—see Example 2.

The PRs may be rhodopsin (+), recoverin (+), PE6a (+) or opsin (+). The opsin may be any of the cone opsins. The PRs may be bipotential for cones or rods. Exemplary photore-ceptors produced by this method may be PAX6−, which may be in contrast to some previously described purported pho-toreceptor cells. As described below in exemplary embodi-ments there is a 2 step differentiation process 1) adding ND medium and retinoic acid and taurine for 2 weeks and 2) use of the photoreceptor differentiation medium, which methods are further exemplified in the working examples below.

In exemplary embodiments the method may produce 40-60 million EFPCs, 60-90 million RNPCs, or 0.5-1 billion PhRPCs per starting 1 million pluripotent cells.

In an exemplary embodiment, the cells may be trans-planted into a rat in need thereof, e.g., an RCS rat, or other animal model of disease (e.g. for night blindness or for color blindness), and the resulting effect on visual function may be detected by the Optomotor response test, ERG, luminance threshold recording and/or the visual center blood flow assay.

Pharmaceutical Preparations

The PRPCs or photoreceptor cells may be formulated with a pharmaceutically acceptable carrier. For example, PRPCs or photoreceptor cells may be administered alone or as a component of a pharmaceutical formulation. The sub-ject compounds may be formulated for administration in any convenient way for use in medicine. Pharmaceutical prepa-rations suitable for administration may comprise the PRPCs or photoreceptor cells, in combination with one or more pharmaceutically acceptable sterile isotonic aqueous or non-aqueous solutions (e.g., balanced salt solution (BSS)), dis-persions, suspensions or emulsions, or sterile powders which may be reconstituted into sterile injectable solutions or dispersions just prior to use, which may contain antioxi-dants, buffers, bacteriostats, solutes or suspending or thick-ening agents. Exemplary pharmaceutical preparations com-prises the PRPCs or photoreceptor cells in combination with ALCON® BSS PLUS® (a balanced salt solution containing, in each mL, sodium chloride 7.14 mg, potassium chloride 0.38 mg, calcium chloride dihydrate 0.154 mg, magnesium chloride hexahydrate 0.2 mg, dibasic sodium phosphate 0.42 mg, sodium bicarbonate 2.1 mg, dextrose 0.92 mg, gluta-thione disulfide (oxidized glutathione) 0.184 mg, hydrochlo-ric acid and/or sodium hydroxide (to adjust pH to approxi-mately 7.4) in water).

When administered, the pharmaceutical preparations for use in this disclosure may be in a pyrogen-free, physiologi-cally acceptable form.

The preparation comprising PRPCS photoreceptor cells used in the methods described herein may be transplanted in a suspension, gel, colloid, slurry, or mixture. Further, the preparation may desirably be encapsulated or injected in a viscous form into the vitreous humor for delivery to the site of retinal or choroidal damage. Also, at the time of injection, cryopreserved PRPCS photoreceptor cells may be resus-pended with commercially available balanced salt solution to achieve the desired osmolality and concentration for administration by subretinal injection. The preparation may be administered to an area of the pericentral macula that was not completely lost to disease, which may promote attach-ment and/or survival of the administered cells.

The PRPCS or photoreceptor cells of the disclosure may be delivered in a pharmaceutically acceptable ophthalmic formulation by intraocular injection. When administering the formulation by intravitreal injection, for example, the solution may be concentrated so that minimized volumes may be delivered. Concentrations for injections may be at any amount that is effective and non-toxic, depending upon the factors described herein. The pharmaceutical prepara-tions of PRPCS or photoreceptor cells for treatment of a patient may be formulated at doses of at least about $10^4$ cells/mL. The PRPCS or photoreceptor cell preparations for treatment of a patient are formulated at doses of at least about $10^3$, $10^4$, $10^5$, $10^6$, $10^7$, $10^8$, $10^9$, or $10^{10}$ PRPCS or photoreceptor cells/mL. For example, the PRPCS or photo-receptor cells may be formulated in a pharmaceutically acceptable carrier or excipient.

The pharmaceutical preparations of PRPCS or photore-ceptor cells described herein may comprise at least about 1,000; 2,000; 3,000; 4,000; 5,000; 6,000; 7,000; 8,000; or 9,000 PRPCS or photoreceptor cells. The pharmaceutical preparations of PRPCS or photoreceptor cells may comprise at least about $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$ $5\times10^{10}$, $6\times10^{10}$, $7\times10^{10}$, $8\times10^{10}$, or $9\times10^{10}$ PRPCS or photoreceptor cells. The phar-maceutical preparations of PRPCS or photoreceptor cells may comprise at least about $1\times10^2$–$1\times10^3$, $1\times10^2$–$1\times10^4$, $1\times10^4$–$1\times10^5$, or $1\times10^3$–$1\times10^6$ PRPCS or photoreceptor cells. The pharmaceutical preparations of PRPCS or photoreceptor cells may comprise at least about 10,000, 20,000, 25,000, 50,000, 75,000, 100,000, 125,000, 150,000, 175,000, 180,000, 185,000, 190,000, or 200,000 PRPCS or photoreceptor cells. For example, the pharmaceutical preparation of PRPCS or photoreceptor cells may comprise at least about 20,000-200,000 PRPCS or photoreceptor cells in a volume at least about 50-200 μL. Further, the pharmaceutical preparation of PRPCS or photoreceptor cells may comprise about 50,000 PRPCS or photoreceptor is in a volume of 150 μL, about 200,000 PRPCS or photoreceptor cells in a volume of 150 μL, or at least about 180,000 PRPCS or photoreceptor cells in a volume at least about 150 μL.

In the aforesaid pharmaceutical preparations and compositions, the number of PRPCS or photoreceptor cells or concentration of PRPCS or photoreceptor cells may be determined by counting viable cells and excluding non-viable cells. For example, non-viable PRPCS or photoreceptor may be detected by failure to exclude a vital dye (such as Trypan Blue), or using a functional assay (such as the ability to adhere to a culture substrate, phagocytosis, etc.). Additionally, the number of PRPCS or photoreceptor cells or concentration of PRPCS or photoreceptor cells may be determined by counting cells that express one or more PRPCS or photoreceptor cell markers and/or excluding cells that express one or more markers indicative of a cell type other than PRPCS or photoreceptor.

The PRPCS or photoreceptor cells may be formulated for delivery in a pharmaceutically acceptable ophthalmic vehicle, such that the preparation is maintained in contact with the ocular surface for a sufficient time period to allow the cells to penetrate the affected regions of the eye, as for example, the anterior chamber, posterior chamber, vitreous body, aqueous humor, vitreous humor, cornea, iris/ciliary, lens, choroid, retina, sclera, suprachoridal space, conjunctiva, subconjunctival space, episcleral space, intracorneal space, epicorneal space, pars plana, surgically-induced avascular regions, or the macula.

The PRPCS or photoreceptor cells may be contained in a sheet of cells. For example, a sheet of cells comprising PRPCS or photoreceptor cells may be prepared by culturing PRPCS or photoreceptor cells on a substrate from which an intact sheet of cells can be released, e.g., a thermoresponsive polymer such as a thermoresponsive poly(N-isopropylacrylamide) (PNIPAAm)-grafted surface, upon which cells adhere and proliferate at the culture temperature, and then upon a temperature shift, the surface characteristics are altered causing release the cultured sheet of cells (e.g., by cooling to below the lower critical solution temperature (LCST) (see da Silva et al., Trends Biotechnol. 2007 Dec.; 25 (12): 577-83; Hsiue et al., Transplantation. 2006 Feb. 15; 81 (3): 473-6; Ide, T. et al. (2006); Biomaterials 27, 607-614, Sumide, T. et al. (2005), FASEB J. 20, 392-394; Nishida, K. et al. (2004), Transplantation 77, 379-385; and Nishida, K. et al. (2004), N. Engl. J. Med. 351, 1187-1196 each of which is incorporated by reference herein in its entirety). The sheet of cells may be adherent to a substrate suitable for transplantation, such as a substrate that may dissolve in vivo when the sheet is transplanted into a host organism, e.g., prepared by culturing the cells on a substrate suitable for transplantation, or releasing the cells from another substrate (such as a thermoresponsive polymer) onto a substrate suitable for transplantation. An exemplary substrate potentially suitable for transplantation may comprise gelatin (see Hsiue et al., supra). Alternative substrates that may be suitable for transplantation include fibrin-based matrixes and others. The sheet of cells may be used in the manufacture of a medicament for the prevention or treatment of a disease of retinal degeneration. The sheet of PRPCS or photoreceptor cells may be formulated for introduction into the eye of a subject in need thereof. For example, the sheet of cells may be introduced into an eye in need thereof by subfoveal membranectomy with transplantation the sheet of PRPCS or photoreceptor cells, or may be used for the manufacture of a medicament for transplantation after subfoveal membranectomy.

The volume of preparation administered according to the methods described herein may be dependent on factors such as the mode of administration, number of PRPCS or photoreceptor cells, age and weight of the patient, and type and severity of the disease being treated. If administered by injection, the volume of a pharmaceutical preparations of PRPCS or photoreceptor cells of the disclosure may be from at least about 1, 1.5, 2, 2.5, 3, 4, or 5 mL. The volume may be at least about 1-2 mL. For example, if administered by injection, the volume of a pharmaceutical preparation of PRPCS or photoreceptor cells of the disclosure may be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67,68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 100, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 μL (microliters). For example, the volume of a preparation of the disclosure may be from at least about 10-50, 20-50, 25-50, or 1-200 μL. The volume of a preparation of the disclosure may be at least about 10, 20, 30, 40, 50, 100, 110, 120, 130, 140, 150, 160, 170, 180, 190, or 200 μL, or higher.

For example, the preparation may comprise at least about $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, or $9 \times 10^4$ PRPCS or photoreceptor cells per μL. The preparation may comprise 2000 PRPCS or PRs per μL, for example, 100,000 PRPCS or photoreceptor cells per 50 μL or 180,000 PRPCS or photoreceptor cells per 90 μL.

The method of treating retinal degeneration may further comprise administration of an immunosuppressant. Immunosuppressants that may be used include but are not limited to anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Ra receptor antibody), everolimus, mycophenolic acid, RITUXIMAB® (anti-CD20 antibody), sirolimus, and tacrolimus. The immunosuppressants may be dosed at least about 1, 2, 4, 5, 6, 7, 8, 9, or 10 mg/kg. When immunosuppressants are used, they may be administered systemically or locally, and they may be administered prior to, concomitantly with, or following administration of the PRPCS or photoreceptor cells. Immunosuppressive therapy may continue for weeks, months, years, or indefinitely following administration of PRPCS or photoreceptor cells. For example, the patient may be administered 5 mg/kg cyclosporin for 6 weeks following administration of the PRPCS or photoreceptor cells.

The method of treatment of retinal degeneration may comprise the administration of a single dose of PRPCS or photoreceptor cells. Also, the methods of treatment described herein may comprise a course of therapy where PRPCS or photoreceptor cells are administered multiple times over some period. Exemplary courses of treatment may comprise weekly, biweekly, monthly, quarterly, biannually, or yearly treatments. Alternatively, treatment may proceed in phases whereby multiple doses are administered initially (e.g., daily doses for the first week), and subsequently fewer and less frequent doses are needed.

If administered by intraocular injection, the PRPCS or photoreceptor cells may be delivered one or more times periodically throughout the life of a patient. For example, the PRPCS or photoreceptor cells may be delivered once per year, once every 6-12 months, once every 3-6 months, once every 1-3 months, or once every 1-4 weeks. Alternatively, more frequent administration may be desirable for certain conditions or disorders. If administered by an implant or device, the PRPCS or photoreceptor cells may be administered one time, or one or more times periodically throughout the lifetime of the patient, as necessary for the particular patient and disorder or condition being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

The methods described herein may further comprise the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

The PRPCs or PRs may be used in the manufacture of a medicament to treat retinal degeneration. The disclosure also encompasses the use of the preparation comprising PRPCs or PRs in the treatment of blindness. For example, the preparations comprising human PRPCs or PRs may be used to treat retinal degeneration associated with a number of vision-altering ailments that result in photoreceptor damage and blindness, such as, diabetic retinopathy, macular degeneration (including age related macular degeneration, e.g., wet age related macular degeneration and dry age related macular degeneration), retinitis pigmentosa, and Stargardt's Disease (fundus flavimaculatus), night blindness and color blindness. The preparation may comprise at least about 5,000-500,000 PRPCs or PRs (e.g., 100,00 PRPCs or PRs) which may be administered to the retina to treat retinal degeneration associated with a number of vision-altering ailments that result in photoreceptor damage and blindness, such as, diabetic retinopathy, macular degeneration (including age related macular degeneration), retinitis pigmentosa, and Stargardt's Disease (fundus flavimaculatus).

The PRPCs or PRs provided herein may be PRPCs or PRs. Note, however, that the human cells may be used in human patients, as well as in animal models or animal patients. For example, the human cells may be tested in mouse, rat, cat, dog, or non-human primate models of retinal degeneration. Additionally, the human cells may be used therapeutically to treat animals in need thereof, such as in veterinary medicine.

The following are examples to illustrate the invention and should not be viewed as limiting the scope of the invention.

Examples

Example 1: Generation of Photoreceptor Progenitor Cells

Human embryonic stem cells were cultured under feeder free conditions in mTESR1 media (Stem Cell Technology) on a Matrigel™ (a soluble preparation from Engelbreth-Holm-Swarm (EHS) mouse sarcoma cells, BD Biosciences) surface. Upon 80-90% confluence, cells were passaged or frozen. Passaging of stem cells was performed using enzymatic (dispase) or non-enzymatic (EDTA-based cell dissociation buffer, Invitrogen) techniques.

Direct differentiation methods were used for generation of eye field progenitor cells, retinal neural progenitor cells, photoreceptor progenitor cells and retinal photoreceptor cells. Formation of embryoid bodies was not required.

The overall method used for photoreceptor development in these examples is schematically illustrated in FIG. 19, which further illustrates the media used at each step of the process.

Based on staining data it was determined that the cells become EFPC between day 7-day30 (indicated by staining done at day 20 which confirmed this cell identity), they become RNPC between day21-day45 (indicated by staining done at day 30), and they become PhRPC between 1-4 month (based on staining done at day 90).

Additionally it was estimated that the timing at which different cell types arose using the methods described in Example 1 were as follows:

Eye Field Progenitors (EFPC): 7-30 days/65%-98% purity

Retinal Neural Progenitors (RNPC): 21-45 days/70%-95% purity

Photoreceptor Progenitors (PhRPs) capable of becoming both rod photoreceptors and cone photoreceptors: 1-4 months/85%-95% purity Photoreceptor Progenitors (PhRPs) thought to have lost or experienced reduction in their capability of becoming rod photoreceptors (but not cone photoreceptors): 5-12 months/85%-95% purity.

Figure 1:
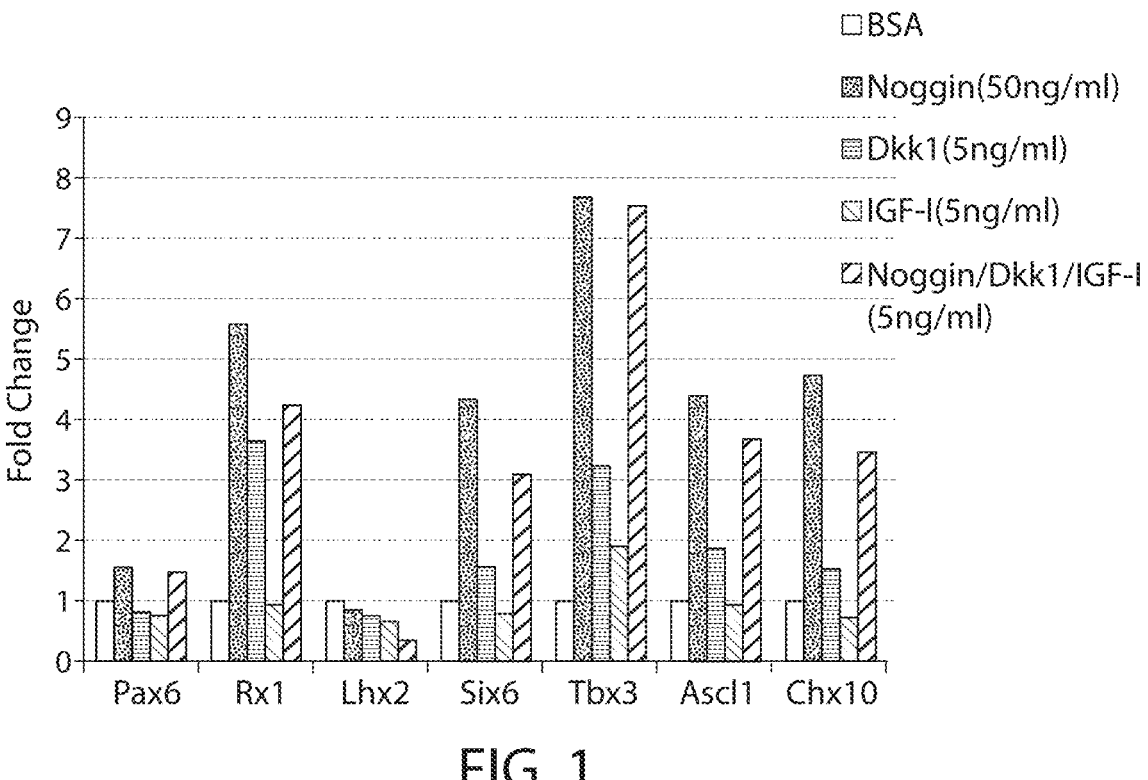
FIG. 1: Real-time PCR analysis of transcripts of eye field transcription factors in cells differentiated under different conditions.

Day 0: Cell differentiation of human pluripotent stem cells was induced at 15-20% confluence. Culture media was changed to retinal induction (RI) medium: DMEM/F12 supplied with 450 mg/ml D-glucose, 100 unit/ml of penicillin, 100 μg/ml of streptomycin, 1% (or optionally 0.1 to 5%) N2 supplement (components listed in FIGS. 21A-21E, Invitrogen), 0.2% (or optionally 0.05-2.0%) B27 supplement, 0.1 mM MEM Non-essential amino acids solution, 25 μg/ml (or optionally 5-50 μg/ml) human insulin was added to the RI medium. The Smad inhibitor Noggin was also included and increased the expression of eye field transcription factors when included at a concentration of 10-100 ng/ml or preferably 50 ng/ml. As shown in FIG. 1, inclusion of different factors including 50 ng/ml Noggin, 5 ng/ml Dkk1, 5 ng/ml IGF-1, or a combination of 5 ng/ml Noggin, 5 ng/ml Dkk1, and 5 ng/ml IGF-1 affected the level of expression of eye field transcription factors in differentiated eye field progenitor cells at day 21. Among those conditions, inclusion of 50 ng/ml Noggin greatly induced the expression of eye field progenitor markers.

The RI medium composition included the following:

N2: 1% (1 ml of N2 per 100 ml media)

B27: 0.2% (0.2 ml of b27 per 100 ml)

Human insulin: 20 μg/ml (in addition to the 5 μg/ml insulin supplied by N2). The final concentration of insulin was 25 μg/ml.

Noggin: 50 ng/ml final concentration.

Figure 2A:
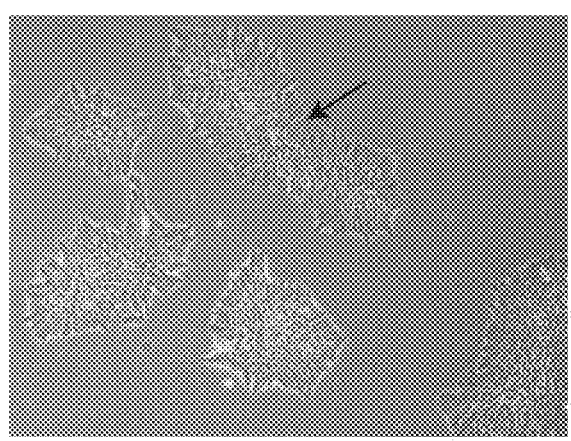
FIGS. 2A-2C: Morphology of differentiating cells.

Day 1-Day 4: A complete media change was done on every day. Though this frequency is preferred, it is thought that changing the medium less often, e.g., every 2-3 days, may be suitable particularly if a larger volume of media is used. Cell colonies continued to grow in the RI media with insulin and Noggin in the same concentrations as in the previous step. After 1 day exposure to RI media, cells located at the colony margin were elongated and column-shaped, as shown in FIG. 2A.

Day 5: Cell cultures became 80-90% confluent on day 5. Media was changed to neural differentiation (ND) medium: Neurobasal Medium (components listed in FIGS. 21A-21E, Invitrogen) supplied with 450 mg/ml D-glucose, 100 unit/ml of penicillin, 100 μg/ml of streptomycin, 1× GlutaMAX™ (a stabilized form dipeptide from L-glutamine, L-alanyl-L-glutamine), 1% (or optionally 0.1 to 5%) N2 supplement (a chemically defined, serum-free supplement based on Bottenstein's N–1 formulation comprising 1 mM Human Transferrin (Holo), 0.0861 mM Insulin Recombinant Full Chain, 0.002 Progesterone, 10.01 mM Putrescine, and 0.00301 mM Selenite, Invitrogen),2% (or optionally 0.05-2.0%) B27 supplement (components listed in FIGS. 21A-21E), 0.1 mM MEM Non-essential amino acids solution. Noggin was also added to the ND media at the final concentration of 50 ng/ml (or optionally 10-100 ng/ml).

Figure 2B:
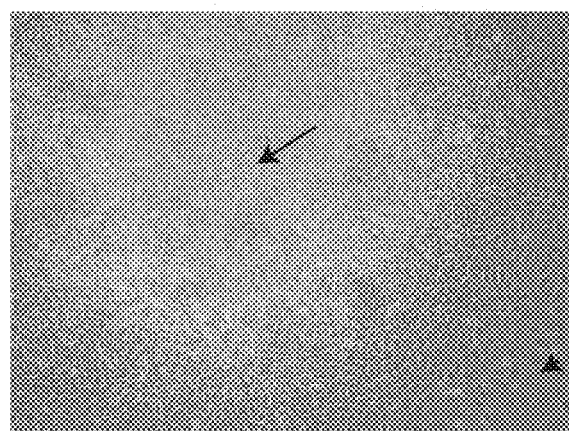
Figure 2C:
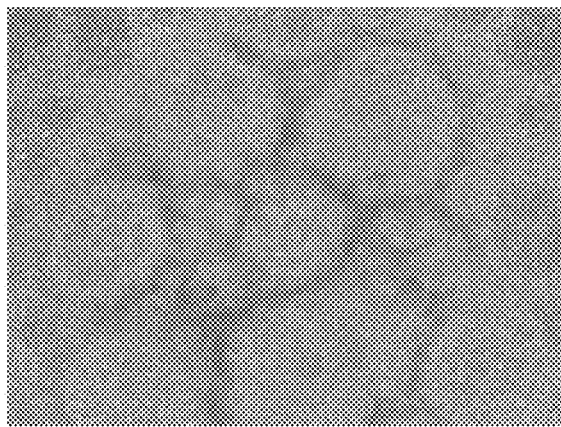
Figure 3A:
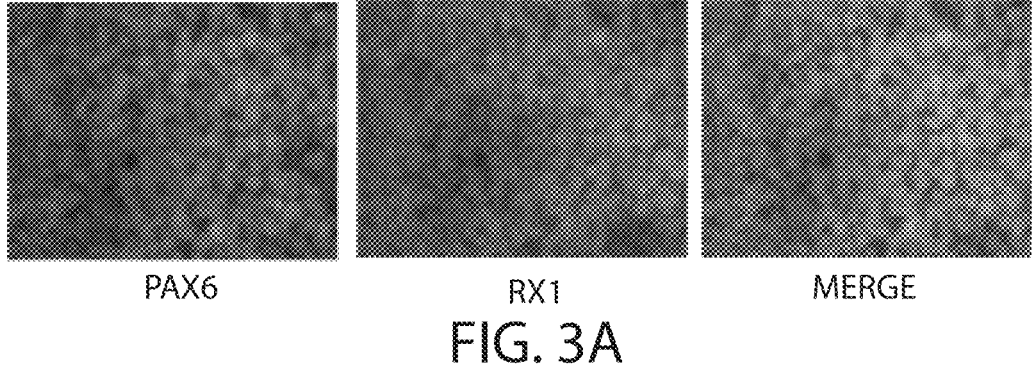
Figure 3B:
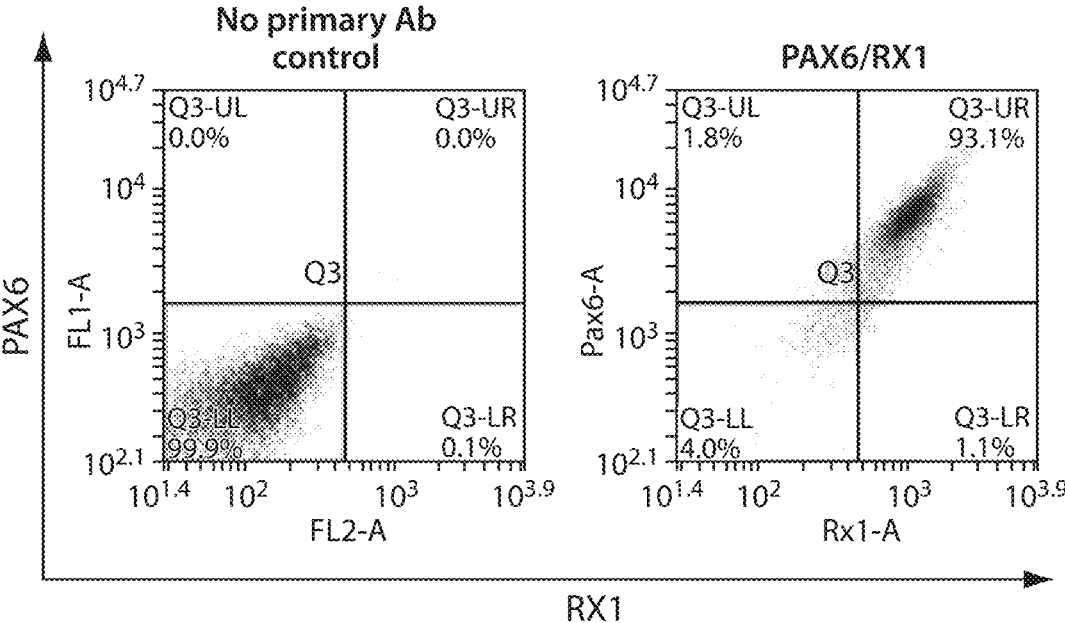

Day 6-Day 20: Cells were maintained in the ND medium. Half the amount of medium was changed every 2 days. Cell colonies continued to grow in the ND medium. The edge cells become flat and large, while the central cells were smaller and formed compact cell clusters (FIG. 2B). Around Day 14, cells located at the center of colonies began to form Rosette-like structures (FIG. 2C). At day 21, over 90% of the cells co-expressed PAX6 and RX1 (FIG. 3A-3B) as revealed by immunostaining and flow cytometry. By immunostaining, cells were positive for Nestin and SOX2 (FIG. 3C-3D). Cells were negative for an ES cell marker (specifically OCT4) and a retinal neural progenitor marker (specifically CHX10). By RT-PCR, cells expressed eye field transcription factors: PAX6, RX1, LHX2, SIX3, SIX6, TBX3 and SOX2 (FIG. 3E). These results indicate that the cells were eye-field progenitor cells.

The cells become eye field progenitors after they are cultured with neural differentiation media, from about day 7-8 (about 2-3 days culture in ND media). At these time points detectable PAX6/rx1 double positive cells arise. After about day 14 (between days 14-30), high purity (>90%) of eye field progenitor are generated.

Between about days 7-30 "Eye Field Progenitor Cells" or "EFPCs" are formed.

Day 21-Day24: At Day 21, cells were lifted off from the growth surface and mechanically fragmented into clusters in ND medium without Noggin. Cell clusters were transferred to 100 mm ultra-low attachment culture dishes. Cell clusters rounded up and formed individual spheres (solid clusters) in the suspension culture. At Day 23, half of the culture medium was replaced.

Figures 4A, 4B, 4C:
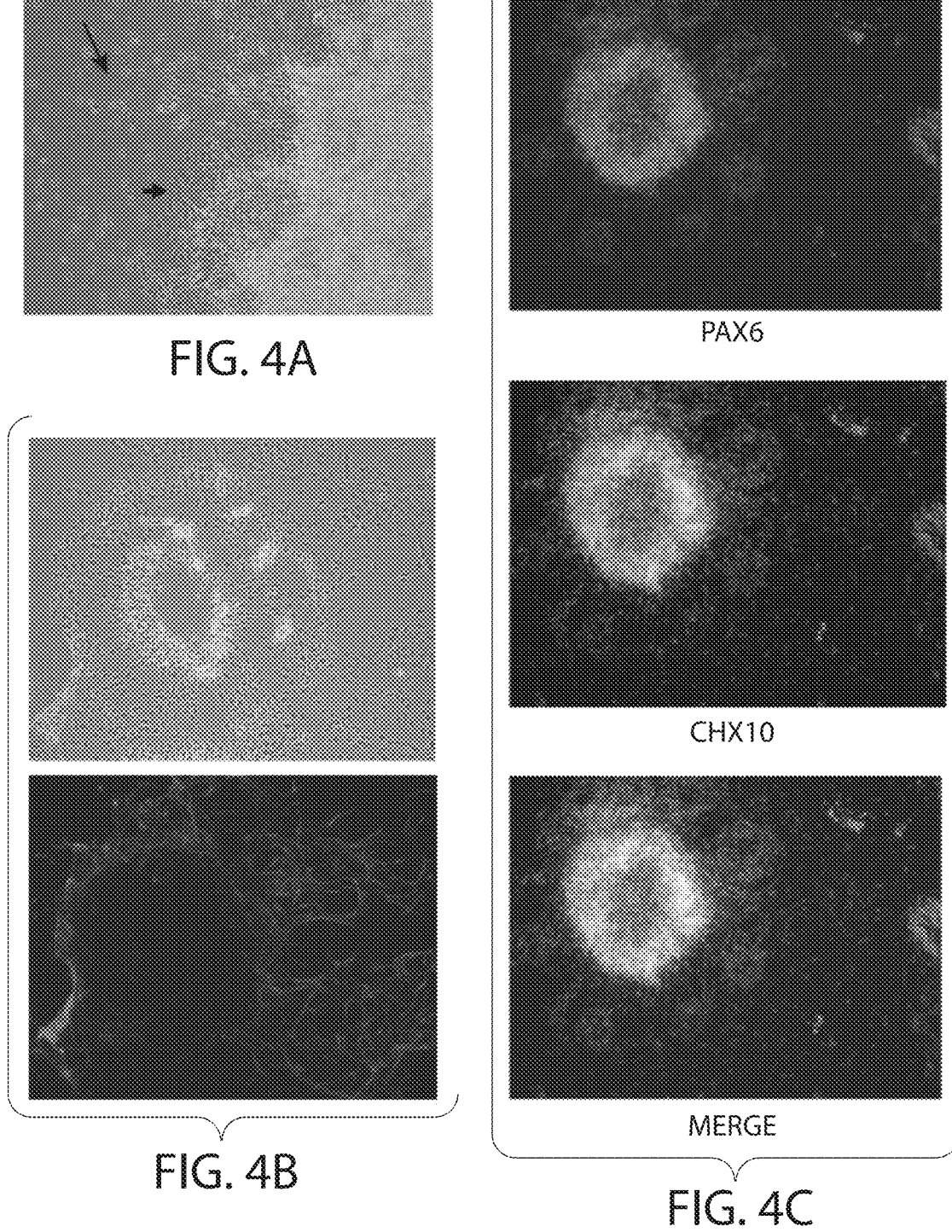
FIGS. 4A-4C: Cells cultured at 30 days after initiation of differentiation expressed retinal neural progenitor markers.

At Day 25, spheres were collected and dead cells and debris were removed by washing the spheres with the ND media. Cell spheres were plated onto Matrigel™ coated glass chamber slide (for immunostaining) or tissue culture dishes in the ND medium. Spheres attached within 12 hours. They continued to grow and show neuronal phenotypes, specifically exhibiting cell aggregates within the spheres that extended axon-like neurites with some cells migrating out from aggregates (FIG. 4A). There were few big epithelial-like cells which could be eliminated during cell passage (see "Month 2-Month 3" below). The cultures were maintained with half of the culture medium changed every two days until the cell cultures become confluent It was observed that balls of spheres attached to the plate.

At Day 30, the migrating cells were positive for Tuj1, which labels immature and mature neurons (FIG. 4B). Cells in the aggregates were negative for Tuj1. Over 95% cells (including cells in the aggregates or migrating out from aggregates) co-expressed PAX6 and CHX10 suggesting that they had become retinal neural progenitors (FIG. 4C).

Month 2-Month 3: Growth and passaging cells in the ND media. The cells from the previous step were passaged when they became confluent. A two-step successive passaging technique was used to produce high-purity neural cultures by eliminating the majority of non-neuronal phenotype cells. The first step: neural sphere culture. Cells were enzymatically (e.g., using Accutase) or mechanically dissociated into a mixture of single cells and cell clusters. Cells were transferred to ultra-low attachment dishes in ND medium. All cells with neuronal phenotype form neural spheres in the suspension culture. On day 3, half of the medium was changed and the cells were maintained until day 5. The second step: adherent culture. Neural spheres were collected on day 5 and dead cells and debris were removed by washing the spheres with ND medium. Spheres were plated on Matrigel™-coated tissue culture dishes until confluent. The first and second steps were alternated and the cells were so maintained until the end of the third month.

Figure 5A:
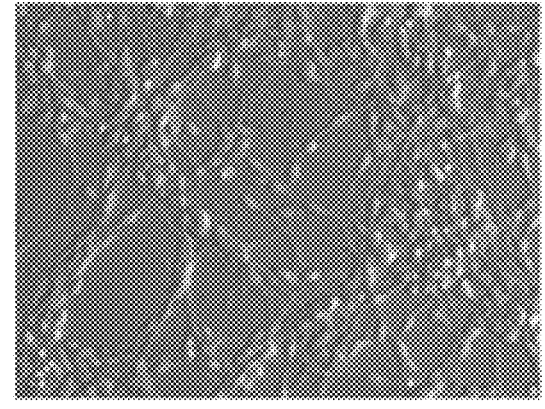
FIGS. 5A-5D: Cells cultured at 3 months after initiation of differentiation.
Figure 5B:
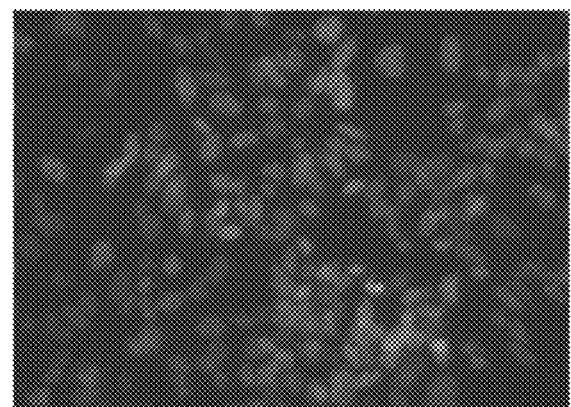
Figure 5C:
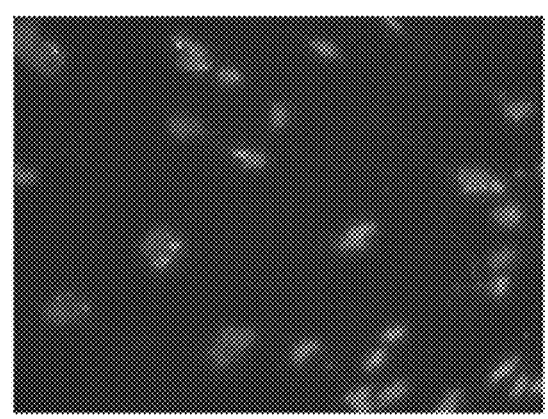
Figure 5D:
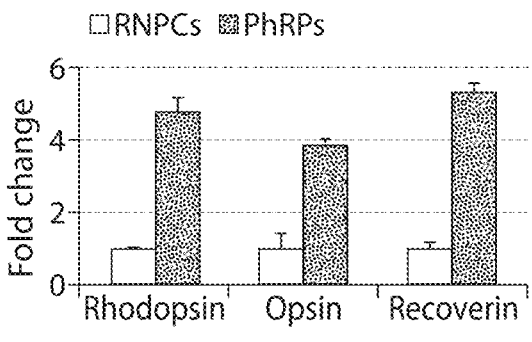
Figure 6A:
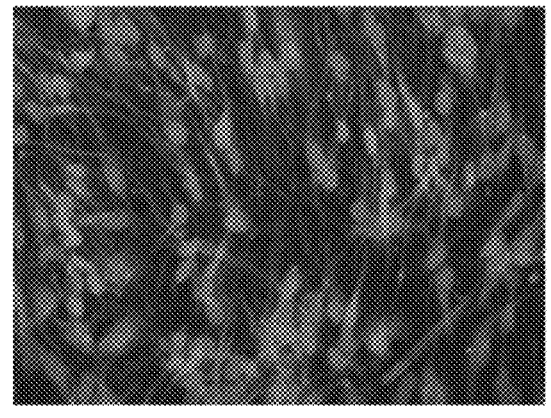
FIGS. 6A-6D: Differentiated cells express photoreceptor cell markers. Cells expressed (FIG. 6A) Rhodopsin, (FIG. 6B) Rhodopsin and Recoverin, (FIG. 6C) Opsin, and (FIG. 6D) phosphodiesterase 6A alpha subunit (PDE6a). DAPI labels cell nuclei.
Figure 6B:
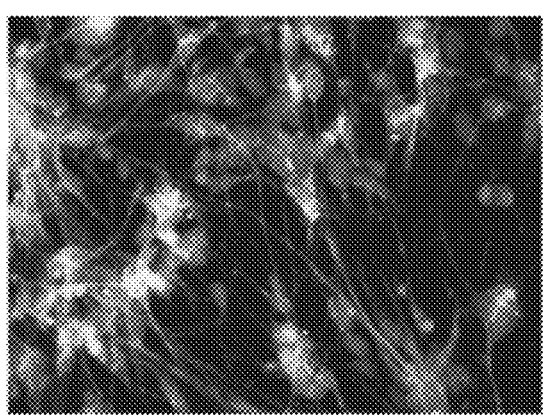
Figure 6C:
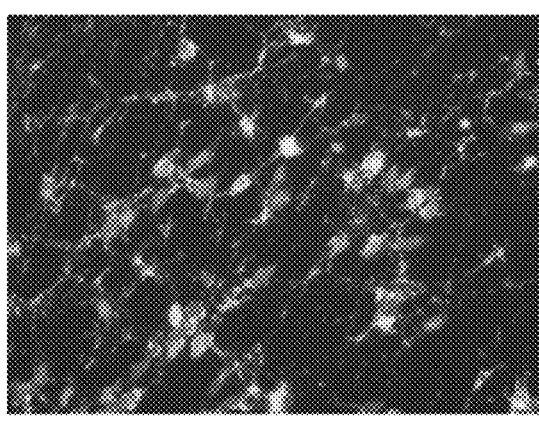
Figure 6D:
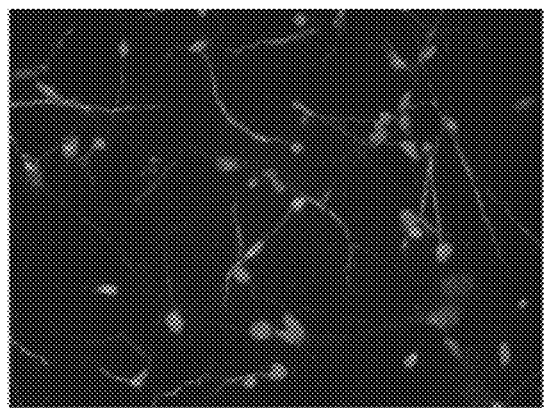

At the end of the 3rd month, the cells showed neural phenotype. Specifically, the cells formed neurites in culture (FIG. 5A). They were capable of proliferation. They expressed PAX6 but were negative for CHX10 as assessed by immunostaining (FIG. 5B). By immunostaining, the cells were positive for Recoverin, which was expressed in the cytoplasm of the cell body (FIG. 5C). The cells also expressed Rhodopsin, Opsin and Recoverin mRNA (FIG. 5D). Real-time PCR analyses revealed that the expressions of transcription factors controlling rod and/or cone photoreceptor differentiation are highly expressed (Table 1). These results indicate that the cells were photoreceptor progenitors. Additionally, at this time-point it was through based on observations that all or essentially all of the cells in the culture are photoreceptor progenitors.

TABLE 1

Quantitative RT-PCT analyses of transcription factors controlling photoreceptor differentiation and regeneration.

| Transcription Factors | Rod/Cone | Fold change (vs. ESC) |
|---|---|---|
| TRβ2 | Cone | 3.5-5 |
| NR2E3 | Rod | 7-11 |
| NRL | Rod | 4-8 |
| MASH1 | Rod | 1000-1200 |
| CRX | Rod, Cone | — |
| RORβ | Rod, Cone | 40-60 |
| OTX2 | Rod, Cone | — |

Month 4-Month 9/or longer: In vitro expansion of photoreceptor progenitors. In some experiments the cells were further expanded using the two-step successive passaging technique described above ("Month 2-Month 3"). However, it was observed that over time the cells lose their capability to differentiate into cone photoreceptors (though they retain the ability to differentiate into rod photoreceptors). Specifically, after photoreceptor progenitors were maintained by the two-step successive passaging technique for 9 months in culture and then induced to differentiate, they only produced cells that expressed rod photoreceptor markers and not cells that expressed cone photoreceptor markers. This property could potentially be put to advantageous use, as progenitor cells that preferentially produce rod photoreceptors may be useful in the treatment of diseases wherein rod formation is desirable, or as a reagent for the study of factors involved in photoreceptor progenitor fate determination.

Example 2: Differentiation of Photoreceptor Progenitor Cells: Cell Treatment with Retinoic Acid and Taurine Attached photoreceptor progenitors were treated with retinoic acid in the following conditions for two weeks: ND medium supplied with 100 ng/ml (or optionally 10-1000 ng/ml) retinoic acid and 100 µM (or optionally 20-500 µM) taurine. Half of the culture medium was changed every 2 days.

Differentiate cells in Photoreceptor differentiation media: The medium was changed to Photoreceptor Differentiation Medium comprising Neurobasal Medium (Invitrogen) supplied with 450 mg/ml D-glucose, 100 unit/ml of penicillin, 100 µg/ml of streptomycin, 1× GlutaMAX™, 1% N2 supplement (Invitrogen), 2% B27 supplement (formula number 080085-SA), with the addition of 5 µM (or optionally 1-100 µM) Forskolin, 10 ng/ml (or optionally 1-100 ng/ml) BDNF, 10 ng/ml (or optionally 1-100 ng/ml) CNTF, 10 ng/ml (or optionally 5-50 ng/ml) LIF and 10 µM (or optionally 1-100 µM) DATP. Half of the medium was changed every 2 days. Specifically the amounts of each factor were as follows: Forskolin (5 µM), BDNF (10 ng/ml), CNTF (10 ng/ml), LIF (10 ng/ml) and DATP (10 µM). LIF was determined not to be necessary and can be left out.

At two weeks after initiating cell differentiation, the expressions of Rhodopsin, Opsin (green/red), Recoverin and phosphodiesterase 6A alpha subunit (PDE6a) were detected in the cytoplasm of the cell body and neurites (FIG. 6A-6D). These gene expression results indicate that these are photoreceptor cells.

Example 3: Cryopreservation of Human ESC-Derived Retinal Neural Progenitors

Retinal neural progenitors of the invention, photoreceptor progenitors of the invention and retinoic acid treated photoreceptor progenitors of the invention can be frozen down in an animal-free cryopreservation buffer, such as Cryostor CS10, or another cryopreservation buffer such as 90% FBS and 10% DMSO. With respect to the photoreceptor progenitors, it was observed that freezing cells as neurospheres was beneficial, which may be due to the benefits of cell-cell contact. Preferably the neurospheres were frozen down at a size that was not too large, such as 50-250 cells.

Example 4: Animal Studies in Stargardt Macular Dystrophy Animal Model

Figure 7:
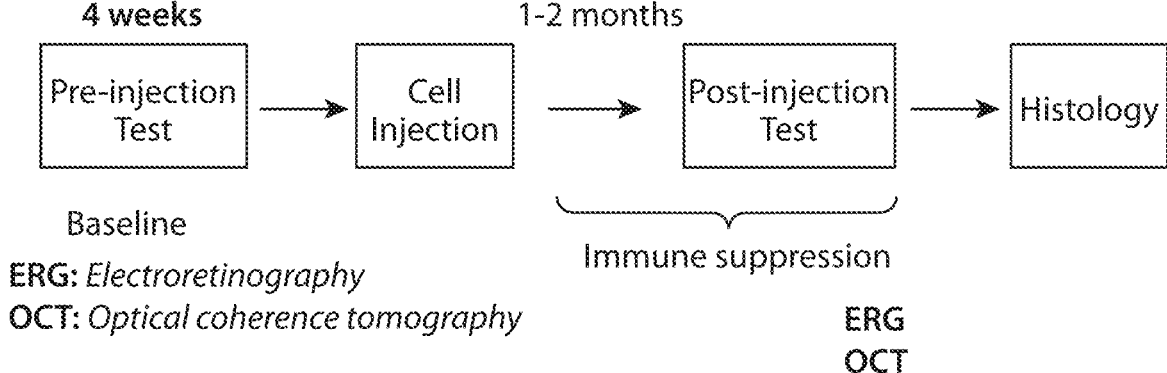
FIG. 7: Schematic diagram of animal studies in ELOVL4-transgenic mice.

Animal studies were carried out in a Stargardt macular dystrophy animal model, ELOVL4 transgenic 2 (TG2) mice (FIG. 7).

Photoreceptor progenitors (produced as described in Example 1) and separately, retinoic acid and taurine treated photoreceptor progenitors (i.e., immature photoreceptor cells, produced as described in Example 2) were dissociated into single cells using Accutase. Cells were re-suspended in PBS buffer.

28 days-old TG2 mice received an injection of 1 µl of cell suspension containing $5\times10^5$ cells into the subretinal space or 150 µl of cell suspension containing $1\times10^6$ cells into the tail vein. All mice underwent baseline ERG and OCT tests before cell injection.

Mice were fed with water supplied with Cyclosporin A (USP modified).

Figure 8:
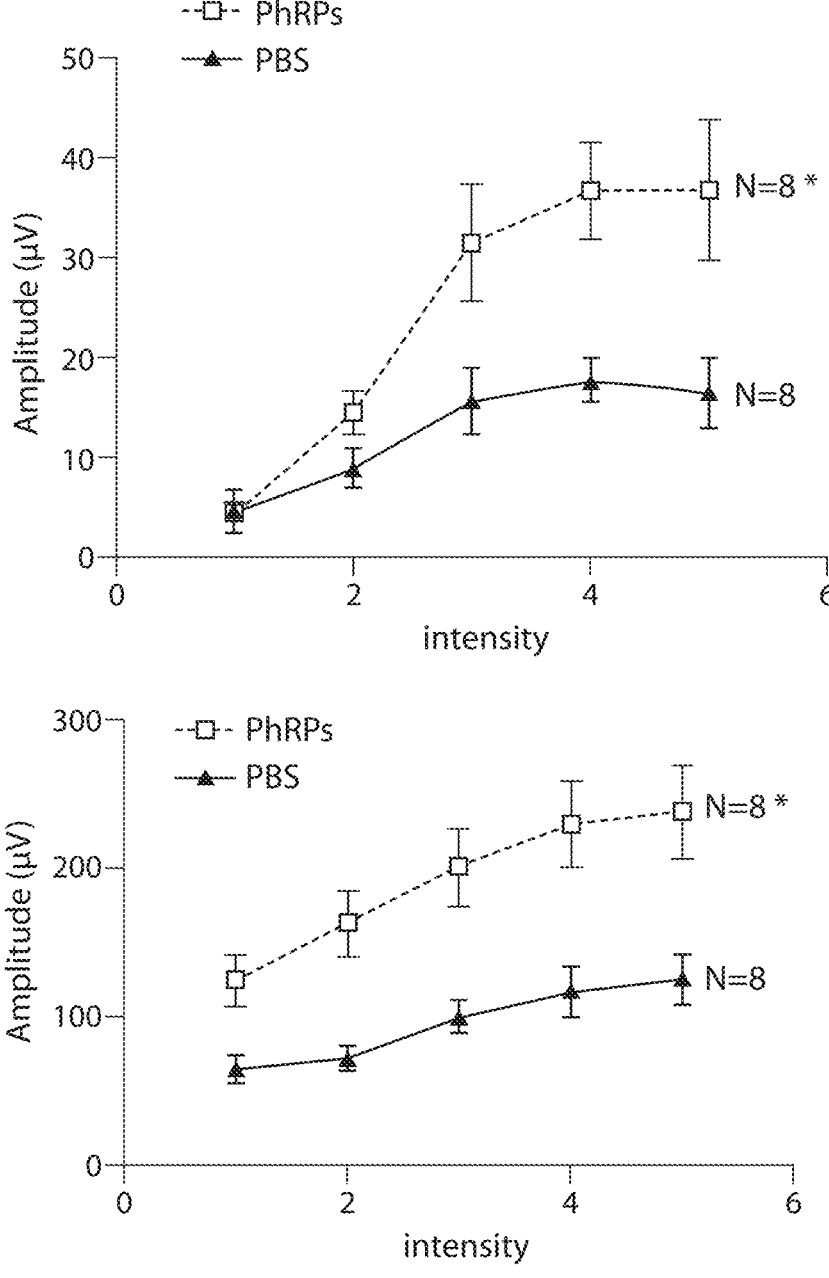
FIG. 8: Scotopic ERG intensity-response function recorded at one month after subretinal cell injection. Stimulus intensity curves for scotopic a-waves (upper panel) and b-waves (lower panel) from ELOVL4-TG2 mice administered PBS (black line) or photoreceptor progenitor cells (indicated as PhRPs, grey line). *, p<0.001 (vs. PBS).
Figure 9:
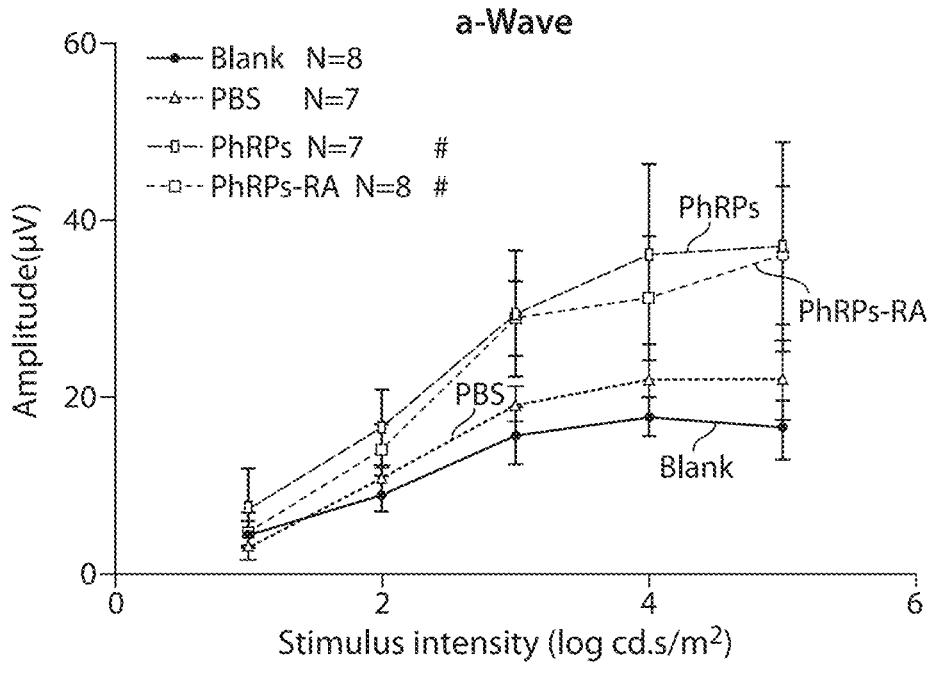
Figure 9:
Figure 9:
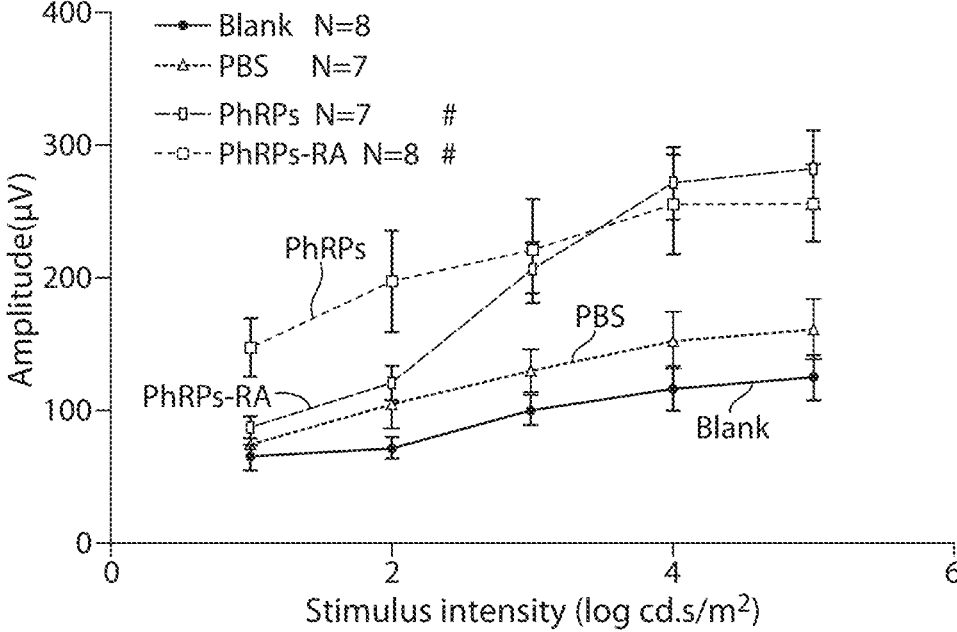

At one month after cell injection, mice that received a subretinal injection of photoreceptor progenitors showed a significant improvement of the rod photoreceptor function revealed by a significant increase of the scotopic ERG amplitude of both the a- and b-wave (FIG. 8). Mice that received a tail vein injection of photoreceptor progenitors and retinoic acid and taurine-treated photoreceptor progenitors showed a significant improvement of the Rod photoreceptor function revealed by a significant increase of the scotopic ERG amplitude of both a- and b-wave (FIG. 9).

At two months after cell injection, mice that received a tail vein injection of retinoic acid treated photoreceptor progenitors showed a further improvement of the rod photoreceptor function revealed by a further increase of the amplitude of both a- and b-wave of scotopic ERG responsive curve (FIG. 10A-10C). The function of cone photoreceptors was significantly improved as revealed by a significant increase of the photopic ERG amplitude of both a- and b-wave (FIG. 11).

At two months after injection, mice that received a tail vein injection of immature photoreceptor cells treated with retinoic acid and taurine showed a significant increase of whole retina thickness revealed by OCT (FIG. 12).

At two months after cell transplantation, there was a significant preservation of photoreceptor neurons in the ONL of retina in mice that received retinoic acid and taurine-treated photoreceptor progenitors (FIG. 13).

Example 5: Animal Models of Achromatopsia (Color Blindness) and Improving Night Vision Cells produced according to the methods described in Example 1 or Example 2 are tested in mouse, sheep, and/or dog models of Achromatopsia (color blindness). The following models are used:

Mouse: (1) the cpfl5 mouse: a naturally occurring mouse model of achromatopsia with a CNGA3 mutation; (2) CNGA3 knockout mice; (3) GNAT2cpfl3 mice: mutation related to GNAT2; (4) PDE6C-cpfl1: mutation related to pde6c.

Sheep: Awassi sheep lambs: mutation in CNGA3

Dog: Two natural occurring canines for mutation in CNGA3 have been identified: the autosomal recessive canine cone degeneration in the Alaskan malamute and the German shorthaired pointer.

Photoreceptor progenitors (produced as described in Example 1) are dissociated into single cells using accutase. Cells and are re-suspended in PBS buffer. The animals receive injections of $2\times10^5$ cells or more into the vitreous cavity or $5\times10^6$ cells or more into a tail vein (e.g., the tail vein). Control animals receive an injection with PBS buffer. After one or two months or at other time points, the animals are given optomotor responsiveness tests to check visual function in order to detect possible improvements thereto.

Additionally, histological analysis is performed to determine whether there is any significant preservation of photoreceptor neurons or growth of photoreceptor neurons, and additionally to detect whether cells transplanted into the vitreous cavity showed good survival after injection, and whether the cells differentiated into rod or cone photoreceptor cells expressing markers thereof.

Example 6: Animal Studies in a Photoreceptor Degeneration Rat Model, Royal College of Surgeons (RCS) Rat Photoreceptor progenitors (produced as described in Example 1) were dissociated into single cells using accutase. Cells were re-suspended in PBS buffer.

On postnatal day 30, RCS rats received injections of $2\times10^5$ cells into the vitreous cavity or $5\times10^6$ cells into the tail vein. Control rats received an injection with PBS buffer.

RCS rats were fed with water supplied with Cyclosporin A (USP modified).

At one month and two months after cell injection, rats were given optomotor responsive tests to check visual function. There was no significant improvement in visual function in treated rats (data not shown).

The resulting effect on visual function may be detected by the Optomotor response test, ERG, luminance threshold recording and/or visual center blood flow assay.

At two months after cell injection, Histology revealed a significant preservation of photoreceptor neurons in the ONL of retina in RCS rats administered with cell treatment (FIG. 15).

Preservation of rod and cone photoreceptor outer segment revealed by immunostaining of Rhodopsin (rod) and Opsin (cone) was observed in cell treated groups (both intravitreal and tail vein injection, FIG. 16 and FIG. 17).

Cells transplanted into the vitreous cavity showed good survival at 2 months after injection, then further differentiated into rod photoreceptor cells expressing rod photoreceptor markers (FIG. 18).

The invention claimed is:

1. A method of differentiating pluripotent stem cells, comprising:
   (a) culturing a preparation of adherent pluripotent stem cells in the presence of a BMP inhibitor to produce PAX6(+), OCT4(−) cells;
   (b) culturing the PAX6(+), OCT4(−) cells in the absence of a BMP inhibitor to produce PAX6(+), CHX10(+) retinal neural progenitor cells; and
   (c) culturing the PAX6(+), CHX10(+) retinal neural progenitor cells as cell aggregates in a suspension culture.

2. The method of claim 1, wherein the pluripotent stem cells are embryonic stem cells or induced pluripotent stem cells.

3. The method of claim 1, wherein the preparation of adherent pluripotent stem cells is cultured in feeder-free conditions.

4. The method of claim 1, wherein the preparation of adherent pluripotent stem cells is cultured in a medium comprising the BMP inhibitor and further comprising at least one of a Wnt inhibitor, a TGFβ inhibitor, or IGF-1.

5. The method of claim 4, wherein the preparation of adherent pluripotent stem cells is cultured in a medium comprising a TGFβ inhibitor, optionally wherein the TGFβ inhibitor is SB431542.

6. The method of claim 4, wherein the preparation of adherent pluripotent stem cells is cultured in a medium comprising a Wnt inhibitor, optionally wherein the Wnt inhibitor is DKK1.

7. The method of claim 4, wherein the preparation of adherent pluripotent stem cells is cultured in a medium comprising a BMP inhibitor, a Wnt inhibitor, and a TGFβ inhibitor.

8. The method of claim 4, wherein the preparation of adherent pluripotent stem cells is cultured in a medium comprising a BMP inhibitor, a Wnt inhibitor, a TGFβ inhibitor, and IGF-1.

9. The method of claim 1, wherein step (a) comprises culturing the adherent pluripotent stem cells in a medium comprising a BMP inhibitor, a Wnt inhibitor, and IGF-1 for 1-10 days.

* * * * *